United States Patent
Kim et al.

(10) Patent No.: US 9,274,113 B2
(45) Date of Patent: Mar. 1, 2016

(54) METHOD FOR SCREENING AN AGENT PREVENTING OR TREATING CANCER USING GLYCYL-TRNA SYNTHETASE AND CADHERIN

(71) Applicant: Medicinal Bioconvergence Research Center, Suwon-si (KR)

(72) Inventors: Sunghoon Kim, Seoul (KR); Min Chul Park, Seoul (KR)

(73) Assignee: Medicinal Bioconvergence Research Center, Suwon-si (KR)

( * ) Notice: Subject to any disclaimer, the term of this patent is extended or adjusted under 35 U.S.C. 154(b) by 0 days.

(21) Appl. No.: 14/249,975

(22) Filed: Apr. 10, 2014

(65) Prior Publication Data

US 2014/0220596 A1 Aug. 7, 2014

(30) Foreign Application Priority Data

Oct. 10, 2011 (KR) .......................... 10-2011-0103306

(51) Int. Cl.
*G01N 33/573* (2006.01)
*G01N 33/68* (2006.01)

(52) U.S. Cl.
CPC .............. *G01N 33/573* (2013.01); *G01N 33/68* (2013.01); *G01N 2333/705* (2013.01); *G01N 2333/9015* (2013.01); *G01N 2500/02* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 5,583,973 | A | 12/1996 | DeLisi et al. |
| 5,612,894 | A | 3/1997 | Wertz |
| 2003/0091669 | A1 | 5/2003 | Wang |
| 2006/0019256 | A1 | 1/2006 | Clarke et al. |
| 2010/0310451 | A1 | 12/2010 | Maret et al. |
| 2011/0256119 | A1 | 10/2011 | Kim et al. |

FOREIGN PATENT DOCUMENTS

| | | |
|---|---|---|
| JP | 2010-519219 | 6/2010 |
| KR | 10-2006-0031809 | 4/2006 |
| KR | 10-2010-0040697 | 4/2010 |
| KR | 10-2011-0046521 | 5/2011 |
| WO | 91/18980 | 12/1991 |
| WO | 93/06121 | 4/1993 |
| WO | 94/08051 | 4/1994 |
| WO | 95/12608 | 5/1995 |
| WO | 95/30642 | 11/1995 |
| WO | 95/35503 | 12/1995 |
| WO | 02/00866 | 1/2002 |

OTHER PUBLICATIONS

International Search Report dated on Mar. 8, 2013 in International Patent Application No. PCT/KR2012/008211.
Quansheng Zhou et al., "Orthogonal use of a human tRNA synthetase active site to achieve multi-functionality.", National Struct Mol Biol. 2010, vol. 17, No. 1, pp. 57-61.
Sampath, et al., "Noncanonical Function of Glutamyl-Prolyl-tRNA Synthetase: Gene-Specific Silencing of Translation", Cell, Oct. 15, 2004, vol. 119, 195-208.
Min Guo, et al., "Functional expansion of human tRNA synthetases achieved by structural inventions",Febs Letters, Nov. 20, 2009, 99.434-442, vol. 584, Europe.
U Kämper, et al., "The mitochondrial tyrosyl-tRNA synthetase of Podospora anserina is a bifunctional enzyme active in protein synthesis and RNA splicing", Molecular and Cellular Biology, Feb. 1992, pp. 499-511, vol. 12, No. 2.
Jordanova, et al., "Disrupted function and axonal distribution of mutant tyrosyl-tRNA synthetase in dominant intermediate Charcot-Marie-Tooth neuropathy", Nature Genetics, Feb. 2006, pp. 197-202, vol. 38, No. 2.
Keisuke Wakasugi, et al., "A human aminoacyl-tRNA synthetase as a regulator of angiogenesis", Proceedings of the National Academy of Sciences of the United States of America, Jan. 8, 2002, pp. 173-177, vol. 99, No. 1.
Leslie A. Nangle,et al., "Charcot—Marie—Tooth disease-associated mutant tRNA synthetases linked to altered dimer interface and neurite distribution defect", Proceedings of the National Academy of Sciences of the United States of America, Jul. 3, 2007, pp. 11239-11244, vol. 104, No. 27.
Sang Gyu Park, et al., "Aminoacyl tRNA synthetases and their connections to disease", Proceedings of the National Academy of Sciences of the United States of America, Aug. 12, 2008, pp. 11043-11049, vol. 105, No. 32.
Wakasugi, et al., "Two Distinct Cytokines Released from a Human Aminoacyl-tRNA Synthetase", Science, Apr. 2, 1999, pp. 147-151, vol. 284.
Yang, et al., "Functional and Crystal Structure Analysis of Active Site Adaptations of a Potent Anti-Angiogenic Human tRNA Synthetase", Structure, Jul. 2007, pp. 793-805, vol. 15.
Park, et al., "Functional expansion of aminoacyl-tRNA synthetases and their interacting factors: new perspectives on housekeepers", TRENDS in Biochemical Sciences, Oct. 2005, pp. 569-574, vol. 30, No. 10.
Edfeldt et al., "Different gene expression profiles in metastasizing midgut carcinoid tumors." Endocrine-Related Cancer, 2011, p. 479-489, vol. 18.
Sancisi et al., "Cadherin 6 is a New RUNX2 Target in TGF-Beta Signalling Pathway", PLoS One, Sep. 12, 2013, p. 1-16, vol. 8 Issue 9.
Xu et al., "Screening and identifcation of significant genes related to tumor metastasis and PSMA in prostate cancer using microarray analysis" Oncology Reports 30, 2013, p. 1920-1928.

*Primary Examiner* — Jacob Cheu
(74) *Attorney, Agent, or Firm* — H.C. Park & Associates, PLC

(57) ABSTRACT

The present invention relates to a novel method of screening an agent for preventing or treating cancer using glycyl-tRNA synthetase (GRS) and cadherin (CDH). More particularly, it relates to a method of screening and test agent which modulates the binding level of GRS or their fragment with CDH. As can be seen foregoing, the present invention relates to a novel use of GRS and CDH and provides a method of screening an agent for preventing or treating cancer. The method may be used for developing novel agent for treatment of various cancer.

8 Claims, 14 Drawing Sheets

A

B

C

SEQUENCE LISTING

```
<160> NUMBER OF SEQ ID NOS: 19

<210> SEQ ID NO 1
<211> LENGTH: 685
<212> TYPE: PRT
<213> ORGANISM: Homo sapiens

<400> SEQUENCE: 1

Met Asp Gly Ala Gly Ala Glu Glu Val Leu Ala Pro Leu Arg Leu Ala
 1               5                  10                  15

Val Arg Gln Gln Gly Asp Leu Val Arg Lys Leu Lys Glu Asp Lys Ala
            20                  25                  30

Pro Gln Val Asp Val Asp Lys Ala Val Ala Glu Leu Lys Ala Arg Lys
        35                  40                  45

Arg Val Leu Glu Ala Lys Glu Leu Ala Leu Gln Pro Lys Asp Asp Ile
    50                  55                  60
```

```
Val Asp Arg Ala Lys Met Glu Asp Thr Leu Lys Arg Phe Phe Tyr
 65                  70                  75                  80

Asp Gln Ala Phe Ala Ile Tyr Gly Gly Val Ser Gly Leu Tyr Asp Phe
                 85                  90                  95

Gly Pro Val Gly Cys Ala Leu Lys Asn Asn Ile Ile Gln Thr Trp Arg
            100                 105                 110

Gln His Phe Ile Gln Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile
        355                 360                 365

Ser Pro Asp Lys Leu Arg Phe Arg Gln His Met Glu Asn Glu Met Ala
    370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
        435                 440                 445

Ala Ile Gly Lys Ala Tyr Lys Lys Asp Ala Lys Leu Val Met Glu Tyr
    450                 455                 460

Leu Ala Ile Cys Asp Glu Cys Tyr Ile Thr Glu Ile Glu Met Leu Leu
465                 470                 475                 480
```

-continued

```
Asn Glu Lys Gly Glu Phe Thr Ile Glu Thr Glu Gly Lys Thr Phe Gln
                485                 490                 495

Leu Thr Lys Asp Met Ile Asn Val Lys Arg Phe Gln Lys Thr Leu Tyr
            500                 505                 510

Val Glu Val Val Pro Asn Val Ile Glu Pro Ser Phe Gly Leu Gly
        515                 520                 525

Arg Ile Met Tyr Thr Val Phe Glu His Thr Phe His Val Arg Glu Gly
    530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
        595                 600                 605

Glu Ile Gly Val Ala Phe Gly Val Thr Ile Asp Phe Asp Thr Val Asn
    610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
            660                 665                 670

Glu Gly Gln Glu Thr Gly Lys Lys Glu Thr Ile Glu Glu
        675                 680                 685

<210> SEQ ID NO 2
<211> LENGTH: 175
<212> TYPE: PRT
<213> ORGANISM: Homo sapiens

<400> SEQUENCE: 2

Leu Tyr Val Glu Glu Val Val Pro Asn Val Ile Glu Pro Ser Phe Gly
  1               5                  10                  15

Leu Gly Arg Ile Met Tyr Thr Val Phe Glu His Thr Phe His Val Arg
             20                  25                  30

Glu Gly Asp Glu Gln Arg Thr Phe Phe Ser Phe Pro Ala Val Val Ala
         35                  40                  45

Pro Phe Lys Cys Ser Val Leu Pro Leu Ser Gln Asn Gln Glu Phe Met
     50                  55                  60

Pro Phe Val Lys Glu Leu Ser Glu Ala Leu Thr Arg His Gly Val Ser
 65                  70                  75                  80

His Lys Val Asp Asp Ser Ser Gly Ser Ile Gly Arg Arg Tyr Ala Arg
                 85                  90                  95

Thr Asp Glu Ile Gly Val Ala Phe Gly Val Thr Ile Asp Phe Asp Thr
            100                 105                 110

Val Asn Lys Thr Pro His Thr Ala Thr Leu Arg Asp Arg Asp Ser Met
        115                 120                 125

Arg Gln Ile Arg Ala Glu Ile Ser Glu Leu Pro Ser Ile Val Gln Asp
    130                 135                 140

Leu Ala Asn Gly Asn Ile Thr Trp Ala Asp Val Glu Ala Arg Tyr Pro
145                 150                 155                 160

Leu Phe Glu Gly Gln Glu Thr Gly Lys Lys Glu Thr Ile Glu Glu
                165                 170                 175
```

<210> SEQ ID NO 3
<211> LENGTH: 2058
<212> TYPE: DNA
<213> ORGANISM: Homo sapiens

<400> SEQUENCE: 3

| | | | | | |
|---|---|---|---|---|---|
| atggacggcg | cggggggctga | ggaggtgctg | gctcctctga | ggctagcagt | gcgccagcag | 60 |
| ggagatcttg | tgcgaaaact | caaagaagat | aaagcacccc | aagtagacgt | agacaaagca | 120 |
| gtggctgagc | tcaaagcccg | caagagggtt | ctggaagcaa | aggagctggc | gttacagccc | 180 |
| aaagatgata | ttgtagaccg | agcaaaaatg | aagataccc | tgaagaggag | gtttttctat | 240 |
| gatcaagctt | ttgctatttta | tggaggtgtt | agtggtctgt | atgactttgg | gccagttggc | 300 |
| tgtgctttga | agaacaatat | tattcagacc | tggaggcagc | actttatcca | agaggaacag | 360 |
| atcctggaga | tcgattgcac | catgctcacc | cctgagccag | ttttaaagac | ctctggccat | 420 |
| gtagacaaat | ttgctgactt | catggtgaaa | gacgtaaaaa | atggagaatg | ttttcgtgct | 480 |
| gaccatctat | taaaagctca | tttacagaaa | ttgatgtctg | ataagaagtg | ttctgtcgaa | 540 |
| aagaaatcag | aaatgaaag | tgttttggcc | cagcttgata | actatggaca | gcaagaactt | 600 |
| gcggatcttt | ttgtgaacta | taatgtaaaa | tctcccatta | ctggaaatga | tctatcccct | 660 |
| ccagtgtctt | ttaacttaat | gttcaagact | tcattgggc | ctggaggaaa | catgcctggg | 720 |
| tacttgagac | cagaaactgc | acaggggatt | ttcttgaatt | tcaaacgact | tttggagttc | 780 |
| aaccaaggaa | agttgccttt | tgctgctgcc | cagattggaa | attcttttag | aaatgagatc | 840 |
| tccccctcgat | ctggactgat | cagagtcaga | gaattcacaa | tggcagaaat | tgagcacttt | 900 |
| gtagatccca | gtgagaaaga | ccaccccaag | ttccagaatg | tggcagacct | tcacctttat | 960 |
| ttgtattcag | caaaagccca | ggtcagcgga | cagtccgctc | ggaaaatgcg | cctgggagat | 1020 |
| gctgttgaac | agggtgtgat | taataacaca | gtattaggct | atttcattgg | ccgcatctac | 1080 |
| ctctacctca | cgaaggttgg | aatatctcca | gataaactcc | gcttccggca | gcacatggag | 1140 |
| aatgagatgg | cccattatgc | ctgtgactgt | tgggatgcag | aatccaaaac | atcctacgtt | 1200 |
| tggattgaga | ttgttggatg | tgctgatcgt | tcctgttatg | acctctcctg | tcatgcacga | 1260 |
| gccaccaaag | tcccacttgt | agctgagaaa | cctctgaaag | aacccaaaac | agtcaatgtt | 1320 |
| gttcagtttg | aacccagtaa | gggagcaatt | ggtaaggcat | ataagaagga | tgcaaaactg | 1380 |
| gtgatggagt | atcttgccat | ttgtgatgag | tgctacatta | cagaaattga | tgctgctg | 1440 |
| aatgagaaag | gggaattcac | aattgaaact | gaagggaaaa | catttcagtt | aacaaaagac | 1500 |
| atgatcaatg | tgaagagatt | ccagaaaaca | ctatatgtgg | aagaagttgt | tccgaatgta | 1560 |
| attgaacctt | ccttcggcct | gggtaggatc | atgtatacgg | tatttgaaca | tacattccat | 1620 |
| gtacgagaag | gagatgaaca | gagaacattc | ttcagtttcc | ctgctgtagt | tgctccattc | 1680 |
| aaatgttccg | tcctcccact | gagccaaaac | caggagttca | tgccatttgt | caaggaatta | 1740 |
| tcggaagccc | tgaccaggca | tggagtatct | cacaaagtag | acgattcctc | tgggtcaatc | 1800 |
| ggaaggcgct | atgccaggac | tgatgagatt | ggcgtggctt | ttggtgtcac | cattgacttt | 1860 |
| gacacagtga | acaagacccc | ccacactgca | actctgaggg | accgtgactc | aatgcggcag | 1920 |
| ataagagcag | agatctctga | gctgcccagc | atagtccaag | acctagccaa | tggcaacatc | 1980 |
| acatgggctg | atgtggaggc | caggtatcct | ctgtttgaag | gcaagagac | tggtaaaaaa | 2040 |
| gagacaatcg | aggaatga | | | | | 2058 |

<210> SEQ ID NO 4
<211> LENGTH: 528
<212> TYPE: DNA
<213> ORGANISM: Homo sapiens

<400> SEQUENCE: 4

```
ctatatgtgg aagaagttgt tccgaatgta attgaacctt ccttcggcct gggtaggatc      60
atgtatacgg tatttgaaca tacattccat gtacgagaag gagatgaaca gagaacattc     120
ttcagtttcc ctgctgtagt tgctccattc aaatgttccg tcctcccact gagccaaaac     180
caggagttca tgccatttgt caaggaatta tcggaagccc tgaccaggca tggagtatct     240
cacaaagtag acgattcctc tgggtcaatc ggaaggcgct atgccaggac tgatgagatt     300
ggcgtggctt ttggtgtcac cattgacttt gacacagtga acaagacccc ccacactgca     360
actctgaggg accgtgactc aatgcggcag ataagagcag agatctctga gctgcccagc     420
atagtccaag acctagccaa tgcaacatc  acatgggctg atgtggaggc caggtatcct     480
ctgtttgaag ggcaagagac tggtaaaaaa gagacaatcg aggaatga               528
```

<210> SEQ ID NO 5
<211> LENGTH: 685
<212> TYPE: PRT
<213> ORGANISM: Homo sapiens

<400> SEQUENCE: 5

```
Met Asp Gly Ala Gly Ala Glu Glu Val Leu Ala Pro Leu Arg Leu Ala
  1               5                  10                  15

Val Arg Gln Gln Gly Asp Leu Val Arg Lys Leu Lys Glu Asp Lys Ala
             20                  25                  30

Pro Gln Val Asp Val Asp Lys Ala Val Ala Glu Leu Lys Ala Arg Lys
         35                  40                  45

Arg Val Leu Glu Ala Lys Glu Leu Ala Leu Gln Pro Lys Asp Asp Ile
     50                  55                  60

Val Asp Arg Ala Lys Met Glu Asp Thr Leu Lys Arg Arg Phe Phe Tyr
 65                  70                  75                  80

Asp Gln Ala Phe Ala Ile Tyr Gly Gly Val Ser Gly Leu Tyr Asp Phe
                 85                  90                  95

Gly Pro Val Gly Cys Ala Leu Lys Asn Asn Ile Ile Gln Thr Trp Arg
            100                 105                 110

Gln His Phe Ile Gln Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Val Ser Phe
    210                 215                 220

Asn Leu Met Phe Lys Thr Phe Ile Gly Pro Gly Gly Asn Met Pro Gly
225                 230                 235                 240
```

-continued

Tyr Leu Arg Pro Glu Thr Ala Gln Gly Ile Phe Leu Asn Phe Lys Arg
                     245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile
        355                 360                 365

Ser Pro Asp Lys Leu Arg Phe Arg Gln His Met Glu Asn Glu Met Ala
    370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
        435                 440                 445

Ala Ile Gly Lys Ala Tyr Lys Lys Asp Ala Lys Leu Val Met Glu Tyr
    450                 455                 460

Leu Ala Ile Cys Asp Glu Cys Tyr Ile Thr Glu Met Glu Met Leu Leu
465                 470                 475                 480

Asn Glu Lys Gly Glu Phe Thr Ile Glu Thr Gly Lys Thr Phe Gln
                485                 490                 495

Leu Thr Lys Asp Met Ile Asn Val Lys Arg Phe Gln Lys Thr Leu Tyr
            500                 505                 510

Val Glu Glu Val Val Pro Asn Val Ile Glu Pro Ser Phe Gly Leu Gly
        515                 520                 525

Arg Ile Met Tyr Thr Val Phe Glu His Thr Phe His Val Arg Glu Gly
    530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
        595                 600                 605

Glu Ile Gly Val Ala Phe Gly Val Thr Ile Asp Phe Asp Thr Val Asn
    610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe

```
                    660                 665                 670
Glu Gly Gln Glu Thr Gly Lys Lys Glu Thr Ile Glu Glu
            675                 680                 685

<210> SEQ ID NO 6
<211> LENGTH: 685
<212> TYPE: PRT
<213> ORGANISM: Homo sapiens

<400> SEQUENCE: 6

Met Asp Gly Ala Gly Ala Glu Val Leu Ala Pro Leu Arg Leu Ala
 1               5                  10                  15

Val Arg Gln Gln Gly Asp Leu Val Arg Lys Leu Lys Glu Asp Lys Ala
                20                  25                  30

Pro Gln Val Asp Val Asp Lys Ala Val Ala Glu Leu Lys Ala Arg Lys
            35                  40                  45

Arg Val Leu Glu Ala Lys Glu Leu Ala Leu Gln Pro Lys Asp Asp Ile
        50                  55                  60

Val Asp Arg Ala Lys Met Glu Asp Thr Leu Lys Arg Arg Phe Phe Tyr
 65                 70                  75                  80

Asp Gln Ala Phe Ala Ile Tyr Gly Gly Val Ser Gly Leu Tyr Asp Phe
                85                  90                  95

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350
```

```
Gly Tyr Phe Ile Gly Arg Ile Tyr Leu Tyr Leu Thr Lys Val Gly Ile
            355                 360                 365

Ser Pro Asp Lys Leu Arg Phe Arg Gln His Met Glu Asn Glu Met Ala
370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
        435                 440                 445

Ala Ile Gly Lys Ala Tyr Lys Lys Asp Ala Lys Leu Val Met Glu Tyr
    450                 455                 460

Leu Ala Ile Cys Asp Glu Cys Tyr Ile Thr Glu Met Glu Met Leu Leu
465                 470                 475                 480

Asn Glu Lys Gly Glu Phe Thr Ile Glu Thr Gly Lys Thr Phe Gln
                485                 490                 495

Leu Thr Lys Asp Met Ile Asn Val Lys Arg Phe Gln Lys Thr Leu Tyr
                500                 505                 510

Val Glu Glu Val Val Pro Asn Val Ile Glu Pro Ser Phe Gly Leu Gly
            515                 520                 525

Arg Ile Met Tyr Thr Val Phe Glu His Thr Phe His Val Arg Glu Gly
        530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
        595                 600                 605

Glu Ile Gly Val Ala Phe Gly Val Thr Ile Asp Phe Asp Thr Val Asn
    610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
            660                 665                 670

Glu Gly Gln Glu Thr Gly Lys Lys Glu Thr Ile Glu Glu
        675                 680                 685

<210> SEQ ID NO 7
<211> LENGTH: 739
<212> TYPE: PRT
<213> ORGANISM: Homo sapiens

<400> SEQUENCE: 7

Met Pro Ser Pro Arg Pro Val Leu Leu Arg Gly Ala Arg Ala Ala Leu
1               5                   10                  15

Leu Leu Leu Leu Pro Pro Arg Leu Leu Ala Arg Pro Ser Leu Leu Leu
            20                  25                  30

Arg Arg Ser Leu Ser Ala Ala Ser Cys Ala Pro Ile Ser Leu Pro Ala
        35                  40                  45
```

```
Ala Ala Ser Arg Ser Ser Met Asp Gly Ala Gly Ala Glu Glu Val Leu
         50                   55                  60

Ala Pro Leu Arg Leu Ala Val Arg Gln Gln Gly Asp Leu Val Arg Lys
 65                  70                  75                  80

Leu Lys Glu Asp Lys Ala Pro Gln Val Asp Val Asp Lys Ala Val Ala
                 85                  90                  95

Glu Leu Lys Ala Arg Lys Arg Val Leu Glu Ala Lys Glu Leu Ala Leu
            100                 105                 110

Gln Pro Lys Asp Asp Ile Val Asp Arg Ala Lys Met Glu Asp Thr Leu
            115                 120                 125

Lys Arg Arg Phe Phe Tyr Asp Gln Ala Phe Ala Ile Tyr Gly Gly Val
        130                 135                 140

Ser Gly Leu Tyr Asp Phe Gly Pro Val Gly Cys Ala Leu Lys Asn Asn
145                 150                 155                 160

Ile Ile Gln Thr Trp Arg Gln His Phe Ile Gln Glu Glu Gln Ile Leu
                165                 170                 175

Glu Ile Asp Cys Thr Met Leu Thr Pro Glu Pro Val Leu Lys Thr Ser
            180                 185                 190

Gly His Val Asp Lys Phe Ala Asp Phe Met Val Lys Asp Val Lys Asn
        195                 200                 205

Gly Glu Cys Phe Arg Ala Asp His Leu Leu Lys Ala His Leu Gln Lys
    210                 215                 220

Leu Met Ser Asp Lys Lys Cys Ser Val Glu Lys Lys Ser Glu Met Glu
225                 230                 235                 240

Ser Val Leu Ala Gln Leu Asp Asn Tyr Gly Gln Gln Glu Leu Ala Asp
                245                 250                 255

Leu Phe Val Asn Tyr Asn Val Lys Ser Pro Ile Thr Gly Asn Asp Leu
            260                 265                 270

Ser Pro Pro Val Ser Phe Asn Leu Met Phe Lys Thr Phe Ile Gly Pro
        275                 280                 285

Gly Gly Asn Met Pro Gly Tyr Leu Arg Pro Glu Thr Ala Gln Gly Ile
    290                 295                 300

Phe Leu Asn Phe Lys Arg Leu Leu Glu Phe Asn Gln Gly Lys Leu Pro
305                 310                 315                 320

Phe Ala Ala Ala Gln Ile Gly Asn Ser Phe Arg Asn Glu Ile Ser Pro
                325                 330                 335

Arg Ser Gly Leu Ile Arg Val Arg Glu Phe Thr Met Ala Glu Ile Glu
            340                 345                 350

His Phe Val Asp Pro Ser Glu Lys Asp His Pro Lys Phe Gln Asn Val
        355                 360                 365

Ala Asp Leu His Leu Tyr Leu Tyr Ser Ala Lys Ala Gln Val Ser Gly
    370                 375                 380

Gln Ser Ala Arg Lys Met Arg Leu Gly Asp Ala Val Glu Gln Gly Val
385                 390                 395                 400

Ile Asn Asn Thr Val Leu Gly Tyr Phe Ile Gly Arg Ile Tyr Leu Tyr
                405                 410                 415

Leu Thr Lys Val Gly Ile Ser Pro Asp Lys Leu Arg Phe Arg Gln His
            420                 425                 430

Met Glu Asn Glu Met Ala His Tyr Ala Cys Asp Cys Trp Asp Ala Glu
        435                 440                 445

Ser Lys Thr Ser Tyr Gly Trp Ile Glu Ile Val Gly Cys Ala Asp Arg
    450                 455                 460
```

```
Ser Cys Tyr Asp Leu Ser Cys His Ala Arg Ala Thr Lys Val Pro Leu
465                 470                 475                 480

Val Ala Glu Lys Pro Leu Lys Glu Pro Lys Thr Val Asn Val Val Gln
                485                 490                 495

Phe Glu Pro Ser Lys Gly Ala Ile Gly Lys Ala Tyr Lys Lys Asp Ala
            500                 505                 510

Lys Leu Val Met Glu Tyr Leu Ala Ile Cys Asp Glu Cys Tyr Ile Thr
        515                 520                 525

Glu Met Glu Met Leu Leu Asn Glu Lys Gly Glu Phe Thr Ile Glu Thr
    530                 535                 540

Glu Gly Lys Thr Phe Gln Leu Thr Lys Asp Met Ile Asn Val Lys Arg
545                 550                 555                 560

Phe Gln Lys Thr Leu Tyr Val Glu Val Val Pro Asn Val Ile Glu
                565                 570                 575

Pro Ser Phe Gly Leu Gly Arg Ile Met Tyr Thr Val Phe Glu His Thr
            580                 585                 590

Phe His Val Arg Glu Gly Asp Glu Gln Arg Thr Phe Phe Ser Phe Pro
        595                 600                 605

Ala Val Val Ala Pro Phe Lys Cys Ser Val Leu Pro Leu Ser Gln Asn
    610                 615                 620

Gln Glu Phe Met Pro Phe Val Lys Glu Leu Ser Glu Ala Leu Thr Arg
625                 630                 635                 640

His Gly Val Ser His Lys Val Asp Asp Ser Gly Ser Ile Gly Arg
                645                 650                 655

Arg Tyr Ala Arg Thr Asp Glu Ile Gly Val Ala Phe Gly Val Thr Ile
            660                 665                 670

Asp Phe Asp Thr Val Asn Lys Thr Pro His Thr Ala Thr Leu Arg Asp
        675                 680                 685

Arg Asp Ser Met Arg Gln Ile Arg Ala Glu Ile Ser Glu Leu Pro Ser
    690                 695                 700

Ile Val Gln Asp Leu Ala Asn Gly Asn Ile Thr Trp Ala Asp Val Glu
705                 710                 715                 720

Ala Arg Tyr Pro Leu Phe Glu Gly Gln Glu Thr Gly Lys Lys Glu Thr
                725                 730                 735

Ile Glu Glu

<210> SEQ ID NO 8
<211> LENGTH: 739
<212> TYPE: PRT
<213> ORGANISM: Homo sapiens

<400> SEQUENCE: 8

Met Pro Ser Pro Arg Pro Val Leu Leu Arg Gly Ala Arg Ala Leu
1               5                   10                  15

Leu Leu Leu Leu Pro Pro Arg Leu Leu Ala Arg Pro Ser Leu Leu Leu
                20                  25                  30

Arg Arg Ser Leu Ser Ala Ala Ser Cys Pro Pro Ile Ser Leu Pro Ala
            35                  40                  45

Ala Ala Ser Arg Ser Ser Met Asp Gly Ala Gly Ala Glu Glu Val Leu
        50                  55                  60

Ala Pro Leu Arg Leu Ala Val Arg Gln Gln Gly Asp Leu Val Arg Lys
65                  70                  75                  80

Leu Lys Glu Asp Lys Ala Pro Gln Val Asp Val Asp Lys Ala Val Ala
                85                  90                  95
```

```
Glu Leu Lys Ala Arg Lys Arg Val Leu Glu Ala Lys Glu Leu Ala Leu
                100                 105                 110

Gln Pro Lys Asp Asp Ile Val Asp Arg Ala Lys Met Glu Asp Thr Leu
            115                 120                 125

Lys Arg Arg Phe Phe Tyr Asp Gln Ala Phe Ala Ile Tyr Gly Gly Val
        130                 135                 140

Ser Gly Leu Tyr Asp Phe Gly Pro Val Gly Cys Ala Leu Lys Asn Asn
145                 150                 155                 160

Ile Ile Gln Thr Trp Arg Gln His Phe Ile Gln Glu Gln Ile Leu
                165                 170                 175

Glu Ile Asp Cys Thr Met Leu Thr Pro Glu Pro Val Leu Lys Thr Ser
                180                 185                 190

Gly His Val Asp Lys Phe Ala Asp Phe Met Val Lys Asp Val Lys Asn
            195                 200                 205

Gly Glu Cys Phe Arg Ala Asp His Leu Leu Lys Ala His Leu Gln Lys
210                 215                 220

Leu Met Ser Asp Lys Lys Cys Ser Val Glu Lys Ser Glu Met Glu
225                 230                 235                 240

Ser Val Leu Ala Gln Leu Asp Asn Tyr Gly Gln Gln Glu Leu Ala Asp
                245                 250                 255

Leu Phe Val Asn Tyr Asn Val Lys Ser Pro Ile Thr Gly Asn Asp Leu
            260                 265                 270

Ser Pro Pro Val Ser Phe Asn Leu Met Phe Lys Thr Phe Ile Gly Pro
        275                 280                 285

Gly Gly Asn Met Pro Gly Tyr Leu Arg Pro Glu Thr Ala Gln Gly Ile
        290                 295                 300

Phe Leu Asn Phe Lys Arg Leu Leu Glu Phe Asn Gln Gly Lys Leu Pro
305                 310                 315                 320

Phe Ala Ala Ala Gln Ile Gly Asn Ser Phe Arg Asn Glu Ile Ser Pro
                325                 330                 335

Arg Ser Gly Leu Ile Arg Val Arg Glu Phe Thr Met Ala Glu Ile Glu
                340                 345                 350

His Phe Val Asp Pro Ser Glu Lys Asp His Pro Lys Phe Gln Asn Val
            355                 360                 365

Ala Asp Leu His Leu Tyr Leu Tyr Ser Ala Lys Ala Gln Val Ser Gly
        370                 375                 380

Gln Ser Ala Arg Lys Met Arg Leu Gly Asp Ala Val Glu Gln Gly Val
385                 390                 395                 400

Ile Asn Asn Thr Val Leu Gly Tyr Phe Ile Gly Arg Ile Tyr Leu Tyr
                405                 410                 415

Leu Thr Lys Val Gly Ile Ser Pro Asp Lys Leu Arg Phe Arg Gln His
            420                 425                 430

Met Glu Asn Glu Met Ala His Tyr Ala Cys Asp Cys Trp Asp Ala Glu
        435                 440                 445

Ser Lys Thr Ser Tyr Gly Trp Ile Glu Ile Val Gly Cys Ala Asp Arg
        450                 455                 460

Ser Cys Tyr Asp Leu Ser Cys His Ala Arg Ala Thr Lys Val Pro Leu
465                 470                 475                 480

Val Ala Glu Lys Pro Leu Lys Glu Pro Lys Thr Val Asn Val Val Gln
                485                 490                 495

Phe Glu Pro Ser Lys Gly Ala Ile Gly Lys Ala Tyr Lys Lys Asp Ala
            500                 505                 510

Lys Leu Val Met Glu Tyr Leu Ala Ile Cys Asp Glu Cys Tyr Ile Thr
```

```
              515                 520                 525
Glu Met Glu Met Leu Asn Glu Lys Gly Glu Phe Thr Ile Glu Thr
530                 535                 540

Glu Gly Lys Thr Phe Gln Leu Thr Lys Asp Met Ile Asn Val Lys Arg
545                 550                 555                 560

Phe Gln Lys Thr Leu Tyr Val Glu Glu Val Pro Asn Val Ile Glu
                    565                 570                 575

Pro Ser Phe Gly Leu Gly Arg Ile Met Tyr Thr Val Phe Glu His Thr
                580                 585                 590

Phe His Val Arg Glu Gly Asp Glu Gln Arg Thr Phe Ser Phe Pro
                595                 600                 605

Ala Val Val Ala Pro Phe Lys Cys Ser Val Leu Pro Leu Ser Gln Asn
610                 615                 620

Gln Glu Phe Met Pro Phe Val Lys Glu Leu Ser Glu Ala Leu Thr Arg
625                 630                 635                 640

His Gly Val Ser His Lys Val Asp Asp Ser Ser Gly Ser Ile Gly Arg
                645                 650                 655

Arg Tyr Ala Arg Thr Asp Glu Ile Gly Val Ala Phe Gly Val Thr Ile
                660                 665                 670

Asp Phe Asp Thr Val Asn Lys Thr Pro His Thr Ala Thr Leu Arg Asp
                675                 680                 685

Arg Asp Ser Met Arg Gln Ile Arg Ala Glu Ile Ser Glu Leu Pro Ser
                690                 695                 700

Ile Val Gln Asp Leu Ala Asn Gly Asn Ile Thr Trp Ala Asp Val Glu
705                 710                 715                 720

Ala Arg Tyr Pro Leu Phe Glu Gly Gln Glu Thr Gly Lys Lys Glu Thr
                    725                 730                 735

Ile Glu Glu

<210> SEQ ID NO 9
<211> LENGTH: 739
<212> TYPE: PRT
<213> ORGANISM: Homo sapiens

<400> SEQUENCE: 9

Met Pro Ser Pro Arg Pro Val Leu Leu Arg Gly Ala Arg Ala Ala Leu
1               5                   10                  15

Leu Leu Leu Leu Pro Pro Arg Leu Leu Ala Arg Pro Ser Leu Leu Leu
                20                  25                  30

Arg Arg Ser Leu Ser Ala Ala Ser Cys Ala Pro Ile Ser Leu Pro Ala
            35                  40                  45

Ala Ala Ser Arg Ser Ser Met Asp Gly Ala Gly Ala Glu Glu Val Leu
        50                  55                  60

Ala Pro Leu Arg Leu Ala Val Arg Gln Gln Gly Asp Leu Val Arg Lys
65                  70                  75                  80

Leu Lys Glu Asp Lys Ala Pro Gln Val Asp Val Asp Lys Ala Val Ala
                85                  90                  95

Glu Leu Lys Ala Arg Lys Arg Val Leu Glu Ala Lys Glu Leu Ala Leu
                100                 105                 110

Gln Pro Lys Asp Asp Ile Val Asp Arg Ala Lys Met Glu Asp Thr Leu
            115                 120                 125

Lys Arg Arg Phe Phe Tyr Asp Gln Ala Phe Ala Ile Tyr Gly Gly Val
        130                 135                 140

Ser Gly Leu Tyr Asp Phe Gly Pro Val Gly Cys Ala Leu Lys Asn Asn
```

```
        145                 150                 155                 160
    Ile Ile Gln Thr Trp Arg Gln His Phe Ile Gln Glu Glu Gln Ile Leu
                    165                 170                 175
    Glu Ile Asp Cys Thr Met Leu Thr Pro Glu Pro Val Leu Lys Thr Ser
                    180                 185                 190
    Gly His Val Asp Lys Phe Ala Asp Phe Met Val Lys Asp Val Lys Asn
                    195                 200                 205
    Gly Glu Cys Phe Arg Ala Asp His Leu Leu Lys Ala His Leu Gln Lys
        210                 215                 220
    Leu Met Ser Asp Lys Lys Cys Ser Val Glu Lys Lys Ser Glu Met Glu
    225                 230                 235                 240
    Ser Val Leu Ala Gln Leu Asp Asn Tyr Gly Gln Glu Leu Ala Asp
                    245                 250                 255
    Leu Phe Val Asn Tyr Asn Val Lys Ser Pro Ile Thr Gly Asn Asp Leu
                    260                 265                 270
    Ser Pro Pro Val Ser Phe Asn Leu Met Phe Lys Thr Phe Ile Gly Pro
                    275                 280                 285
    Gly Gly Asn Met Pro Gly Tyr Leu Arg Pro Glu Thr Ala Gln Gly Ile
        290                 295                 300
    Phe Leu Asn Phe Lys Arg Leu Leu Glu Phe Asn Gln Gly Lys Leu Pro
    305                 310                 315                 320
    Phe Ala Ala Ala Gln Ile Gly Asn Ser Phe Arg Asn Glu Ile Ser Pro
                    325                 330                 335
    Arg Ser Gly Leu Ile Arg Val Arg Glu Phe Thr Met Ala Glu Ile Glu
                    340                 345                 350
    His Phe Val Asp Pro Ser Glu Lys Asp His Pro Lys Phe Gln Asn Val
                    355                 360                 365
    Ala Asp Leu His Leu Tyr Leu Tyr Ser Ala Lys Ala Gln Val Ser Gly
        370                 375                 380
    Gln Ser Ala Arg Lys Met Arg Leu Gly Asp Ala Val Glu Gln Gly Val
    385                 390                 395                 400
    Ile Asn Asn Thr Val Leu Gly Tyr Phe Ile Gly Arg Ile Tyr Leu Tyr
                    405                 410                 415
    Leu Thr Lys Val Gly Ile Ser Pro Asp Lys Leu Arg Phe Arg Gln His
                    420                 425                 430
    Met Glu Asn Glu Met Ala His Tyr Ala Cys Asp Cys Trp Asp Ala Glu
                    435                 440                 445
    Ser Lys Thr Ser Tyr Gly Trp Ile Glu Ile Val Gly Cys Ala Asp Arg
        450                 455                 460
    Ser Cys Tyr Asp Leu Ser Cys His Ala Arg Ala Thr Lys Val Pro Leu
    465                 470                 475                 480
    Val Ala Glu Lys Pro Leu Lys Glu Pro Lys Thr Val Asn Val Val Gln
                    485                 490                 495
    Phe Glu Pro Ser Lys Gly Ala Ile Gly Lys Ala Tyr Lys Lys Asp Ala
                    500                 505                 510
    Lys Leu Val Met Glu Tyr Leu Ala Ile Cys Asp Glu Cys Tyr Ile Thr
                    515                 520                 525
    Glu Met Glu Met Leu Leu Asn Glu Lys Gly Glu Phe Thr Ile Glu Thr
                    530                 535                 540
    Glu Gly Lys Thr Phe Gln Leu Thr Lys Asp Met Ile Asn Val Lys Arg
    545                 550                 555                 560
    Phe Gln Lys Thr Leu Tyr Val Glu Glu Val Val Pro Asn Val Ile Glu
                    565                 570                 575
```

-continued

Pro Ser Phe Gly Leu Gly Arg Ile Met Tyr Thr Val Phe Glu His Thr
                580                 585                 590

Phe His Val Arg Glu Gly Asp Glu Gln Arg Thr Phe Phe Ser Phe Pro
            595                 600                 605

Ala Val Val Ala Pro Phe Lys Cys Ser Val Leu Pro Leu Ser Gln Asn
        610                 615                 620

Gln Glu Phe Met Pro Phe Val Lys Glu Leu Ser Glu Ala Leu Thr Arg
625                 630                 635                 640

His Gly Val Ser His Lys Val Asp Asp Ser Gly Ser Ile Gly Arg
                645                 650                 655

Arg Tyr Ala Arg Thr Asp Glu Ile Gly Val Ala Phe Gly Val Thr Ile
            660                 665                 670

Asp Phe Asp Thr Val Asn Lys Thr Pro His Thr Ala Thr Leu Arg Asp
        675                 680                 685

Arg Asp Ser Met Arg Gln Ile Arg Ala Glu Ile Ser Glu Leu Pro Ser
    690                 695                 700

Ile Val Gln Asp Leu Ala Asn Gly Asn Ile Thr Trp Ala Asp Val Glu
705                 710                 715                 720

Ala Arg Tyr Pro Leu Phe Glu Gly Gln Glu Thr Gly Lys Lys Glu Thr
                725                 730                 735

Ile Glu Glu

<210> SEQ ID NO 10
<211> LENGTH: 739
<212> TYPE: PRT
<213> ORGANISM: Homo sapiens

<400> SEQUENCE: 10

Met Pro Ser Pro Arg Pro Val Leu Leu Arg Gly Ala Arg Ala Ala Leu
1               5                   10                  15

Leu Leu Leu Leu Pro Pro Arg Leu Leu Ala Arg Pro Ser Leu Leu Leu
            20                  25                  30

Arg Arg Ser Leu Ser Ala Ala Ser Cys Ala Pro Ile Ser Leu Pro Ala
        35                  40                  45

Ala Ala Ser Arg Ser Ser Met Asp Gly Ala Gly Ala Glu Glu Val Leu
    50                  55                  60

Ala Pro Leu Arg Leu Ala Val Arg Gln Gln Gly Asp Leu Val Arg Lys
65                  70                  75                  80

Leu Lys Glu Asp Lys Ala Pro Gln Val Asp Val Asp Lys Ala Val Ala
                85                  90                  95

Glu Leu Lys Ala Arg Lys Arg Val Leu Glu Ala Lys Glu Leu Ala Leu
            100                 105                 110

Gln Pro Lys Asp Asp Ile Val Asp Arg Ala Lys Met Glu Asp Thr Leu
        115                 120                 125

Lys Arg Arg Phe Phe Tyr Asp Gln Ala Phe Ala Ile Tyr Gly Gly Val
    130                 135                 140

Ser Gly Leu Tyr Asp Phe Gly Pro Val Gly Cys Ala Leu Lys Asn Asn
145                 150                 155                 160

Ile Ile Gln Thr Trp Arg Gln His Phe Ile Gln Glu Glu Gln Ile Leu
                165                 170                 175

Glu Ile Asp Cys Thr Met Leu Thr Pro Glu Pro Val Leu Lys Thr Ser
            180                 185                 190

Gly His Val Asp Lys Phe Ala Asp Phe Met Val Lys Asp Val Lys Asn
        195                 200                 205

```
Gly Glu Cys Phe Arg Ala Asp His Leu Leu Lys Ala His Leu Gln Lys
    210                 215                 220

Leu Met Ser Asp Lys Lys Cys Ser Val Glu Lys Lys Ser Glu Met Glu
225                 230                 235                 240

Ser Val Leu Ala Gln Leu Asp Asn Tyr Gly Gln Gln Glu Leu Ala Asp
                245                 250                 255

Leu Phe Val Asn Tyr Asn Val Lys Ser Pro Ile Thr Gly Asn Asp Leu
                260                 265                 270

Ser Pro Pro Val Ser Phe Asn Leu Met Phe Lys Thr Phe Ile Gly Pro
            275                 280                 285

Gly Gly Asn Met Pro Gly Tyr Leu Arg Pro Glu Thr Ala Gln Gly Ile
    290                 295                 300

Phe Leu Asn Phe Lys Arg Leu Leu Glu Phe Asn Gln Gly Lys Leu Pro
305                 310                 315                 320

Phe Ala Ala Ala Gln Ile Gly Asn Ser Phe Arg Asn Glu Ile Ser Pro
                325                 330                 335

Arg Ser Gly Leu Ile Arg Val Arg Glu Phe Thr Met Ala Glu Ile Glu
                340                 345                 350

His Phe Val Asp Pro Ser Glu Lys Asp His Pro Lys Phe Gln Asn Val
            355                 360                 365

Ala Asp Leu His Leu Tyr Leu Tyr Ser Ala Lys Ala Gln Val Ser Gly
    370                 375                 380

Gln Ser Ala Arg Lys Met Arg Leu Gly Asp Ala Val Glu Gln Gly Val
385                 390                 395                 400

Ile Asn Asn Thr Val Leu Gly Tyr Phe Ile Gly Arg Ile Tyr Leu Tyr
                405                 410                 415

Leu Thr Lys Val Gly Ile Ser Pro Asp Lys Leu Arg Phe Arg Gln His
            420                 425                 430

Met Glu Asn Glu Met Ala His Tyr Ala Cys Asp Cys Trp Asp Ala Glu
    435                 440                 445

Ser Lys Thr Ser Tyr Gly Trp Ile Glu Ile Val Gly Cys Ala Asp Arg
450                 455                 460

Ser Cys Tyr Asp Leu Ser Cys His Ala Arg Ala Thr Lys Val Pro Leu
465                 470                 475                 480

Val Ala Glu Lys Pro Leu Lys Glu Pro Lys Thr Val Asn Val Val Gln
                485                 490                 495

Phe Glu Pro Ser Lys Gly Ala Ile Gly Lys Ala Tyr Lys Lys Asp Ala
                500                 505                 510

Lys Leu Val Met Glu Tyr Leu Ala Ile Cys Asp Glu Cys Tyr Ile Thr
            515                 520                 525

Glu Met Glu Met Leu Leu Asn Glu Lys Gly Glu Phe Thr Ile Glu Thr
    530                 535                 540

Glu Gly Lys Thr Phe Gln Leu Thr Lys Asp Met Ile Asn Val Lys Arg
545                 550                 555                 560

Phe Gln Lys Thr Leu Tyr Val Glu Glu Val Pro Asn Val Ile Glu
                565                 570                 575

Pro Ser Phe Gly Leu Gly Arg Ile Met Tyr Thr Val Phe Glu His Thr
            580                 585                 590

Phe His Val Arg Glu Gly Asp Glu Gln Arg Thr Phe Phe Ser Phe Pro
    595                 600                 605

Ala Val Val Ala Pro Phe Lys Cys Ser Val Leu Pro Leu Ser Gln Asn
610                 615                 620
```

```
Gln Glu Phe Met Pro Phe Val Lys Glu Leu Ser Glu Ala Leu Thr Arg
625                 630                 635                 640

His Gly Val Ser His Lys Val Asp Asp Ser Gly Ser Ile Gly Arg
                645                 650                 655

Arg Tyr Ala Arg Thr Asp Glu Ile Gly Val Ala Phe Gly Val Thr Ile
                660                 665                 670

Asp Phe Asp Thr Val Asn Lys Thr Pro His Thr Ala Thr Leu Arg Asp
                675                 680                 685

Arg Asp Ser Met Arg Gln Ile Arg Ala Glu Ile Ser Glu Leu Pro Ser
                690                 695                 700

Ile Val Gln Asp Leu Ala Asn Gly Asn Ile Thr Trp Ala Asp Val Glu
705                 710                 715                 720

Ala Arg Tyr Pro Leu Phe Glu Gly Gln Glu Thr Gly Lys Lys Glu Thr
                725                 730                 735

Ile Glu Glu

<210> SEQ ID NO 11
<211> LENGTH: 164
<212> TYPE: PRT
<213> ORGANISM: Homo sapiens

<400> SEQUENCE: 11

Leu Tyr Val Glu Glu Val Val Pro Asn Val Ile Glu Pro Ser Phe Gly
1               5                   10                  15

Leu Gly Arg Ile Met Tyr Thr Val Phe Glu His Thr Phe His Val Arg
                20                  25                  30

Glu Gly Asp Glu Gln Arg Thr Phe Ser Phe Pro Ala Val Val Ala
                35                  40                  45

Pro Phe Lys Cys Ser Val Leu Pro Leu Ser Gln Asn Gln Glu Phe Met
    50                  55                  60

Pro Phe Val Lys Glu Leu Ser Glu Ala Leu Thr Arg His Gly Val Ser
65                  70                  75                  80

His Lys Val Asp Asp Ser Ser Gly Ser Ile Gly Arg Arg Tyr Ala Arg
                85                  90                  95

Thr Asp Glu Ile Gly Val Ala Phe Gly Val Thr Ile Asp Phe Asp Thr
                100                 105                 110

Val Asn Lys Thr Pro His Thr Ala Thr Leu Arg Asp Arg Asp Ser Met
                115                 120                 125

Arg Gln Ile Arg Ala Glu Ile Ser Glu Leu Pro Ser Ile Val Gln Asp
130                 135                 140

Leu Ala Asn Gly Asn Ile Thr Trp Ala Asp Val Glu Ala Arg Tyr Pro
145                 150                 155                 160

Leu Phe Glu Gly

<210> SEQ ID NO 12
<211> LENGTH: 663
<212> TYPE: PRT
<213> ORGANISM: Homo sapiens

<400> SEQUENCE: 12

Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
                20                  25                  30

Ala Lys Lys Arg Ala Leu Glu Leu Ser Gly Asn Ser Lys Asn Glu Leu
                35                  40                  45
```

```
Asn Arg Ser Lys Arg Ser Trp Met Trp Asn Gln Phe Phe Leu Leu Glu
     50                  55                  60

Glu Tyr Thr Gly Ser Asp Tyr Gln Tyr Val Gly Lys Leu His Ser Asp
 65                  70                  75                  80

Gln Asp Arg Gly Asp Gly Ser Leu Lys Tyr Ile Leu Ser Gly Asp Gly
                 85                  90                  95

Ala Gly Asp Leu Phe Ile Ile Asn Glu Asn Thr Gly Asp Ile Gln Ala
                100                 105                 110

Thr Lys Arg Leu Asp Arg Glu Glu Lys Pro Val Tyr Ile Leu Arg Ala
            115                 120                 125

Gln Ala Ile Asn Arg Arg Thr Gly Arg Pro Val Glu Pro Glu Ser Glu
        130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
                180                 185                 190

Asn Ser Ala Lys Val Val Tyr Ser Ile Leu Gln Gly Gln Pro Tyr Phe
            195                 200                 205

Ser Val Glu Ser Glu Thr Gly Ile Ile Lys Thr Ala Leu Leu Asn Met
210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Gly Thr Pro Ile Gly
        275                 280                 285

Arg Ile Lys Ala Ser Asp Ala Asp Val Gly Glu Asn Ala Glu Ile Glu
290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
450                 455                 460
```

```
Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
    530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
        595                 600                 605

Thr Gly Leu Ser Thr Gly Ala Leu Val Ala Ile Leu Leu Cys Ile Val
    610                 615                 620

Ile Leu Leu Gly Lys Leu Val Leu Pro Ala Ser Tyr Leu Pro Met Val
625                 630                 635                 640

Arg Gly Ser His Cys Tyr Cys Asp Thr Leu Asp Leu Ser Ala Ser Pro
                645                 650                 655

Ile Lys Ala Tyr Ser Leu Ile
            660

<210> SEQ ID NO 13
<211> LENGTH: 790
<212> TYPE: PRT
<213> ORGANISM: Homo sapiens

<400> SEQUENCE: 13

Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
                20                  25                  30

Ala Lys Lys Arg Ala Leu Glu Leu Ser Gly Asn Ser Lys Asn Glu Leu
            35                  40                  45

Asn Arg Ser Lys Arg Ser Trp Met Trp Asn Gln Phe Phe Leu Leu Glu
        50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175
```

```
Phe Val Val Gln Val Thr Ala Thr Asp Ala Asp Pro Thr Tyr Gly
            180                 185                 190
Asn Ser Ala Lys Val Val Tyr Ser Ile Leu Gln Gly Gln Pro Tyr Phe
            195                 200                 205
Ser Val Glu Ser Glu Thr Gly Ile Ile Lys Thr Ala Leu Leu Asn Met
210                 215                 220
Asp Arg Glu Asn Arg Glu Gln Tyr Gln Val Val Ile Gln Ala Lys Asp
225                 230                 235                 240
Met Gly Gly Gln Met Gly Gly Leu Ser Gly Thr Thr Val Asn Ile
                245                 250                 255
Thr Leu Thr Asp Val Asn Asp Asn Pro Pro Arg Phe Pro Gln Ser Thr
            260                 265                 270
Tyr Gln Phe Lys Thr Pro Glu Ser Ser Pro Gly Thr Pro Ile Gly
            275                 280                 285
Arg Ile Lys Ala Ser Asp Ala Asp Val Gly Glu Asn Ala Glu Ile Glu
            290                 295                 300
Tyr Ser Ile Thr Asp Gly Glu Gly Leu Asp Met Phe Asp Val Ile Thr
305                 310                 315                 320
Asp Gln Glu Thr Gln Glu Gly Ile Ile Thr Val Lys Lys Leu Leu Asp
                325                 330                 335
Phe Glu Lys Lys Lys Val Tyr Thr Leu Lys Val Glu Ala Ser Asn Pro
            340                 345                 350
Tyr Val Glu Pro Arg Phe Leu Tyr Leu Gly Pro Phe Lys Asp Ser Ala
            355                 360                 365
Thr Val Arg Ile Val Val Glu Asp Val Asp Glu Pro Pro Val Phe Ser
            370                 375                 380
Lys Leu Ala Tyr Ile Leu Gln Ile Arg Glu Asp Ala Gln Ile Asn Thr
385                 390                 395                 400
Thr Ile Gly Ser Val Thr Ala Gln Asp Pro Asp Ala Ala Arg Asn Pro
                405                 410                 415
Val Lys Tyr Ser Val Asp Arg His Thr Asp Met Asp Arg Ile Phe Asn
            420                 425                 430
Ile Asp Ser Gly Asn Gly Ser Ile Phe Thr Ser Lys Leu Leu Asp Arg
            435                 440                 445
Glu Thr Leu Leu Trp His Asn Ile Thr Val Ile Ala Thr Glu Ile Asn
            450                 455                 460
Asn Pro Lys Gln Ser Ser Arg Val Pro Leu Tyr Ile Lys Val Leu Asp
465                 470                 475                 480
Val Asn Asp Asn Ala Pro Glu Phe Ala Glu Phe Tyr Glu Thr Phe Val
                485                 490                 495
Cys Glu Lys Ala Lys Ala Asp Gln Leu Ile Gln Thr Leu His Ala Val
            500                 505                 510
Asp Lys Asp Asp Pro Tyr Ser Gly His Gln Phe Ser Phe Ser Leu Ala
            515                 520                 525
Pro Glu Ala Ala Ser Gly Ser Asn Phe Thr Ile Gln Asp Asn Lys Asp
            530                 535                 540
Asn Thr Ala Gly Ile Leu Thr Arg Lys Asn Gly Tyr Asn Arg His Glu
545                 550                 555                 560
Met Ser Thr Tyr Leu Leu Pro Val Val Ile Ser Asp Asn Asp Tyr Pro
                565                 570                 575
Val Gln Ser Ser Thr Gly Thr Val Thr Val Arg Val Cys Ala Cys Asp
            580                 585                 590
```

His His Gly Asn Met Gln Ser Cys His Ala Glu Ala Leu Ile His Pro
595                 600                 605

Thr Gly Leu Ser Thr Gly Ala Leu Val Ala Ile Leu Leu Cys Ile Val
610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
            645                 650                 655

Val Ser Tyr Asn Asp Glu Gly Gly Gly Glu Asp Thr Gln Ala Phe
            660                 665                 670

Asp Ile Gly Thr Leu Arg Asn Pro Glu Ala Ile Glu Asp Asn Lys Leu
            675                 680                 685

Arg Arg Asp Ile Val Pro Glu Ala Leu Phe Leu Pro Arg Arg Thr Pro
690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
            725                 730                 735

Thr Tyr Ala Tyr Glu Gly Thr Gly Ser Val Ala Asp Ser Leu Ser Ser
            740                 745                 750

Leu Glu Ser Val Thr Thr Asp Ala Asp Gln Asp Tyr Asp Tyr Leu Ser
            755                 760                 765

Asp Trp Gly Pro Arg Phe Lys Lys Leu Ala Asp Met Tyr Gly Gly Val
770                 775                 780

Asp Ser Asp Lys Asp Ser
785                 790

<210> SEQ ID NO 14
<211> LENGTH: 790
<212> TYPE: PRT
<213> ORGANISM: Homo sapiens

<400> SEQUENCE: 14

Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
        35                  40                  45

Asn Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
            85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
            165                 170                 175

-continued

```
Phe Val Val Gln Val Thr Ala Thr Asp Ala Asp Pro Thr Tyr Gly
            180                 185                 190

Asn Ser Ala Lys Val Val Tyr Ser Ile Leu Gln Gly Gln Pro Tyr Phe
            195                 200                 205

Ser Val Glu Ser Glu Thr Gly Ile Ile Lys Thr Ala Leu Leu Asn Met
210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Val Asn Ile
            245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Gly Thr Pro Ile Gly
            275                 280                 285

Arg Ile Lys Ala Ser Asp Ala Asp Val Gly Glu Asn Ala Glu Ile Glu
            290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
            325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
            355                 360                 365

Thr Val Arg Ile Val Val Glu Asp Val Asp Glu Pro Pro Val Phe Ser
            370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
            405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
            435                 440                 445

Glu Thr Leu Leu Trp His Asn Ile Thr Val Ile Ala Thr Glu Ile Asn
450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
            485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
            515                 520                 525

Pro Glu Ala Ala Ser Gly Ser Asn Phe Thr Ile Gln Asp Asn Lys Asp
            530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
            565                 570                 575

Val Gln Ser Ser Thr Gly Thr Val Thr Val Arg Val Cys Ala Cys Asp
            580                 585                 590
```

```
His His Gly Asn Met Gln Ser Cys His Ala Glu Ala Leu Ile His Pro
            595                 600                 605

Thr Gly Leu Ser Thr Gly Ala Leu Val Ala Ile Leu Leu Cys Ile Val
610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655

Val Ser Tyr Asn Asp Glu Gly Gly Glu Asp Thr Gln Ala Phe
            660                 665                 670

Asp Ile Gly Thr Leu Arg Asn Pro Glu Ala Ile Glu Asp Asn Lys Leu
            675                 680                 685

Arg Arg Asp Ile Val Pro Glu Ala Leu Phe Leu Pro Arg Arg Thr Pro
690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750

Leu Glu Ser Val Thr Thr Asp Ala Asp Gln Asp Tyr Asp Tyr Leu Ser
            755                 760                 765

Asp Trp Gly Pro Arg Phe Lys Lys Leu Ala Asp Met Tyr Gly Gly Val
770                 775                 780

Asp Ser Asp Lys Asp Ser
785                 790

<210> SEQ ID NO 15
<211> LENGTH: 790
<212> TYPE: PRT
<213> ORGANISM: Homo sapiens

<400> SEQUENCE: 15

Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
        35                  40                  45

Asn Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175
```

-continued

```
Phe Val Val Gln Val Thr Ala Thr Asp Ala Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Val Asn Ile
                245                 250                 255

Thr Leu Thr Asp Val Asn Asp Asn Pro Pro Arg Phe Pro Gln Ser Thr
                260                 265                 270

Tyr Gln Phe Lys Thr Pro Glu Ser Ser Pro Gly Thr Pro Ile Gly
        275                 280                 285

Arg Ile Lys Ala Ser Asp Ala Asp Val Gly Glu Asn Ala Glu Ile Glu
        290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
    450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
    530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590
```

```
His His Gly Asn Met Gln Ser Cys His Ala Glu Ala Leu Ile His Pro
            595                 600                 605

Thr Gly Leu Ser Thr Gly Ala Leu Val Ala Ile Leu Leu Cys Ile Val
610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655

Val Ser Tyr Asn Asp Glu Gly Gly Glu Glu Asp Thr Gln Ala Phe
            660                 665                 670

Asp Ile Gly Thr Leu Arg Asn Pro Glu Ala Ile Glu Asp Asn Lys Leu
        675                 680                 685

Arg Arg Asp Ile Val Pro Glu Ala Leu Phe Leu Pro Arg Arg Thr Pro
690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750

Leu Glu Ser Val Thr Thr Asp Ala Asp Gln Asp Tyr Asp Tyr Leu Ser
        755                 760                 765

Asp Trp Gly Pro Arg Phe Lys Lys Leu Ala Asp Met Tyr Gly Gly Val
770                 775                 780

Asp Ser Asp Lys Asp Ser
785                 790

<210> SEQ ID NO 16
<211> LENGTH: 790
<212> TYPE: PRT
<213> ORGANISM: Homo sapiens

<400> SEQUENCE: 16

Met Lys Ile Thr Ser Thr Ser Cys Ile Cys Pro Val Leu Val Cys Leu
1               5                   10                  15

Cys Phe Val Gln Arg Cys Tyr Gly Thr Ala His Ser Ser Ile Lys
            20                  25                  30

Val Met Arg Asn Gln Thr Lys His Ile Glu Gly Glu Thr Glu Val His
        35                  40                  45

His Arg Pro Lys Arg Gly Trp Val Trp Asn Gln Phe Phe Val Leu Glu
    50                  55                  60

Glu His Met Gly Pro Asp Pro Gln Tyr Val Gly Lys Leu His Ser Asn
65                  70                  75                  80

Ser Asp Lys Gly Asp Gly Ser Val Lys Tyr Ile Leu Thr Gly Glu Gly
                85                  90                  95

Ala Gly Thr Ile Phe Ile Ile Asp Asp Thr Thr Gly Asp Ile His Ser
            100                 105                 110

Thr Lys Ser Leu Asp Arg Glu Gln Lys Thr His Tyr Val Leu His Ala
        115                 120                 125

Gln Ala Ile Asp Arg Arg Thr Asn Lys Pro Leu Glu Pro Glu Ser Glu
    130                 135                 140

Phe Ile Ile Lys Val Gln Asp Ile Asn Asp Asn Ala Pro Lys Phe Thr
145                 150                 155                 160

Asp Gly Pro Tyr Ile Val Thr Val Pro Glu Met Ser Asp Met Gly Thr
                165                 170                 175
```

```
Ser Val Leu Gln Val Thr Ala Thr Asp Ala Asp Pro Thr Tyr Gly
            180                 185                 190

Asn Ser Ala Arg Val Val Tyr Ser Ile Leu Gln Gly Gln Pro Tyr Phe
            195                 200                 205

Ser Val Asp Pro Lys Thr Gly Val Ile Arg Thr Ala Leu His Asn Met
210                 215                 220

Asp Arg Glu Ala Arg Glu His Tyr Ser Val Val Ile Gln Ala Lys Asp
225                 230                 235                 240

Met Ala Gly Gln Val Gly Leu Ser Gly Ser Thr Val Asn Ile
                245                 250                 255

Thr Leu Thr Asp Val Asn Asp Asn Pro Pro Arg Phe Pro Gln Lys His
            260                 265                 270

Tyr Gln Leu Tyr Val Pro Glu Ser Ala Gln Val Gly Ser Ala Val Gly
            275                 280                 285

Lys Ile Lys Ala Asn Asp Ala Asp Thr Gly Ser Asn Ala Asp Met Thr
290                 295                 300

Tyr Ser Ile Ile Asn Gly Asp Gly Met Gly Ile Phe Ser Ile Ser Thr
305                 310                 315                 320

Asp Lys Glu Thr Arg Glu Gly Ile Leu Ser Leu Lys Lys Pro Leu Asn
            325                 330                 335

Tyr Glu Lys Lys Lys Ser Tyr Thr Leu Asn Ile Glu Gly Ala Asn Thr
            340                 345                 350

His Leu Asp Phe Arg Phe Ser His Leu Gly Pro Phe Lys Asp Ala Thr
            355                 360                 365

Met Leu Lys Ile Ile Val Gly Asp Val Asp Glu Pro Pro Leu Phe Ser
            370                 375                 380

Met Pro Ser Tyr Leu Met Glu Val Tyr Glu Asn Ala Lys Ile Gly Thr
385                 390                 395                 400

Val Val Gly Thr Val Leu Ala Gln Asp Pro Asp Ser Thr Asn Ser Leu
            405                 410                 415

Val Arg Tyr Phe Ile Asn Tyr Asn Val Glu Asp Asp Arg Phe Phe Asn
            420                 425                 430

Ile Asp Ala Asn Thr Gly Thr Ile Arg Thr Thr Lys Val Leu Asp Arg
            435                 440                 445

Glu Glu Thr Pro Trp Tyr Asn Ile Thr Val Thr Ala Ser Glu Ile Asp
450                 455                 460

Asn Pro Asp Leu Leu Ser His Val Thr Val Gly Ile Arg Val Leu Asp
465                 470                 475                 480

Val Asn Asp Asn Pro Pro Glu Leu Ala Arg Glu Tyr Asp Ile Ile Val
            485                 490                 495

Cys Glu Asn Ser Lys Pro Gly Gln Val Ile His Thr Ile Ser Ala Thr
            500                 505                 510

Asp Lys Asp Asp Phe Ala Asn Gly Pro Arg Phe Asn Phe Phe Leu Asp
            515                 520                 525

Glu Arg Leu Pro Val Asn Pro Asn Phe Thr Leu Lys Asp Asn Glu Asp
            530                 535                 540

Asn Thr Ala Ser Ile Leu Thr Arg Arg Arg Phe Ser Arg Thr Val
545                 550                 555                 560

Gln Asp Val Tyr Tyr Leu Pro Ile Met Ile Ser Asp Gly Gly Ile Pro
            565                 570                 575

Ser Leu Ser Ser Ser Thr Leu Thr Ile Arg Val Cys Ala Cys Glu
            580                 585                 590
```

```
Arg Asp Gly Arg Val Arg Thr Cys His Ala Glu Ala Phe Leu Ser Ser
            595                 600                 605

Ala Gly Leu Ser Thr Gly Ala Leu Ile Ala Ile Leu Leu Cys Val Leu
610                 615                 620

Ile Leu Leu Ala Ile Val Val Leu Phe Ile Thr Leu Arg Arg Ser Lys
625                 630                 635                 640

Lys Glu Pro Leu Ile Ile Ser Glu Glu Asp Val Arg Glu Asn Val Val
                645                 650                 655

Thr Tyr Asp Asp Glu Gly Gly Gly Glu Asp Thr Glu Ala Phe Asp
            660                 665                 670

Ile Thr Ala Leu Arg Asn Pro Ser Ala Ala Glu Glu Leu Lys Tyr Arg
            675                 680                 685

Arg Asp Ile Arg Pro Glu Val Lys Leu Thr Pro Arg His Gln Thr Ser
690                 695                 700

Ser Thr Leu Glu Ser Ile Asp Val Gln Glu Phe Ile Lys Gln Arg Leu
705                 710                 715                 720

Ala Glu Ala Asp Leu Asp Pro Ser Val Pro Pro Tyr Asp Ser Leu Gln
                725                 730                 735

Thr Tyr Ala Tyr Glu Gly Gln Arg Ser Glu Ala Gly Ser Ile Ser Ser
            740                 745                 750

Leu Asp Ser Ala Thr Thr Gln Ser Asp Gln Asp Tyr His Tyr Leu Gly
            755                 760                 765

Asp Trp Gly Pro Glu Phe Lys Lys Leu Ala Glu Leu Tyr Gly Glu Ile
            770                 775                 780

Glu Ser Glu Arg Thr Thr
785                 790

<210> SEQ ID NO 17
<211> LENGTH: 1159
<212> TYPE: PRT
<213> ORGANISM: Homo sapiens

<400> SEQUENCE: 17

Met Tyr Leu Ser Ile Cys Cys Cys Phe Leu Leu Trp Ala Pro Ala Leu
  1               5                  10                  15

Thr Leu Lys Asn Leu Asn Tyr Ser Val Pro Glu Glu Gln Gly Ala Gly
                20                  25                  30

Thr Val Ile Gly Asn Ile Gly Arg Asp Ala Arg Leu Gln Pro Gly Leu
            35                  40                  45

Pro Pro Ala Glu Arg Gly Gly Gly Arg Ser Lys Ser Gly Ser Tyr
    50                  55                  60

Arg Val Leu Glu Asn Ser Ala Pro His Leu Leu Asp Val Asp Ala Asp
65                  70                  75                  80

Ser Gly Leu Leu Tyr Thr Lys Gln Arg Ile Asp Arg Glu Ser Leu Cys
                85                  90                  95

Arg His Asn Ala Lys Cys Gln Leu Ser Leu Glu Val Phe Ala Asn Asp
            100                 105                 110

Lys Glu Ile Cys Met Ile Lys Val Glu Ile Gln Asp Ile Asn Asp Asn
            115                 120                 125

Ala Pro Ser Phe Ser Ser Asp Gln Ile Glu Met Asp Ile Ser Glu Asn
130                 135                 140

Ala Ala Pro Gly Thr Arg Phe Pro Leu Thr Ser Ala His Asp Pro Asp
145                 150                 155                 160

Ala Gly Glu Asn Gly Leu Arg Thr Tyr Leu Leu Thr Arg Asp Asp His
                165                 170                 175
```

```
Gly Leu Phe Gly Leu Asp Val Lys Ser Arg Gly Asp Gly Thr Lys Phe
            180                 185                 190

Pro Glu Leu Val Ile Gln Lys Ala Leu Asp Arg Glu Gln Gln Asn His
            195                 200                 205

His Thr Leu Val Leu Thr Ala Leu Asp Gly Gly Glu Pro Pro Arg Ser
210                 215                 220

Ala Thr Val Gln Ile Asn Val Lys Val Ile Asp Ser Asn Asp Asn Ser
225                 230                 235                 240

Pro Val Phe Glu Ala Pro Ser Tyr Leu Val Glu Leu Pro Glu Asn Ala
                245                 250                 255

Pro Leu Gly Thr Val Val Ile Asp Leu Asn Ala Thr Ala Asp Glu
            260                 265                 270

Gly Pro Asn Gly Glu Val Leu Tyr Ser Phe Ser Ser Tyr Val Pro Asp
            275                 280                 285

Arg Val Arg Glu Leu Phe Ser Ile Asp Pro Lys Thr Gly Leu Ile Arg
            290                 295                 300

Val Lys Gly Asn Leu Asp Tyr Glu Glu Asn Gly Met Leu Glu Ile Asp
305                 310                 315                 320

Val Gln Ala Arg Asp Leu Gly Pro Asn Pro Ile Pro Ala His Cys Lys
                325                 330                 335

Val Thr Val Lys Leu Ile Asp Arg Asn Asp Asn Ala Pro Ser Ile Gly
            340                 345                 350

Phe Val Ser Val Arg Gln Gly Ala Leu Ser Glu Ala Ala Pro Pro Gly
            355                 360                 365

Thr Val Ile Ala Leu Val Arg Val Thr Asp Arg Asp Ser Gly Lys Asn
            370                 375                 380

Gly Gln Leu Gln Cys Arg Val Leu Gly Gly Gly Thr Gly Gly Gly
385                 390                 395                 400

Gly Gly Leu Gly Gly Pro Gly Gly Ser Val Pro Phe Lys Leu Glu Glu
            405                 410                 415

Asn Tyr Asp Asn Phe Tyr Thr Val Val Thr Asp Arg Pro Leu Asp Arg
            420                 425                 430

Glu Thr Gln Asp Glu Tyr Asn Val Thr Ile Val Ala Arg Asp Gly Gly
            435                 440                 445

Ser Pro Pro Leu Asn Ser Thr Lys Ser Phe Ala Ile Lys Ile Leu Asp
450                 455                 460

Glu Asn Asp Asn Pro Pro Arg Phe Thr Lys Gly Leu Tyr Val Leu Gln
465                 470                 475                 480

Val His Glu Asn Asn Ile Pro Gly Glu Tyr Leu Gly Ser Val Leu Ala
                485                 490                 495

Gln Asp Pro Asp Leu Gly Gln Asn Gly Thr Val Ser Tyr Ser Ile Leu
            500                 505                 510

Pro Ser His Ile Gly Asp Val Ser Ile Tyr Thr Tyr Val Ser Val Asn
            515                 520                 525

Pro Thr Asn Gly Ala Ile Tyr Ala Leu Arg Ser Phe Asn Phe Glu Gln
            530                 535                 540

Thr Lys Ala Phe Glu Phe Lys Val Leu Ala Lys Asp Ser Gly Ala Pro
545                 550                 555                 560

Ala His Leu Glu Ser Asn Ala Thr Val Arg Val Thr Val Leu Asp Val
                565                 570                 575

Asn Asp Asn Ala Pro Val Ile Val Leu Pro Thr Leu Gln Asn Asp Thr
            580                 585                 590
```

```
Ala Glu Leu Gln Val Pro Arg Asn Ala Gly Leu Gly Tyr Leu Val Ser
            595                 600                 605

Thr Val Arg Ala Leu Asp Ser Asp Phe Gly Glu Ser Gly Arg Leu Thr
610                 615                 620

Tyr Glu Ile Val Asp Gly Asn Asp Asp His Leu Phe Glu Ile Asp Pro
625                 630                 635                 640

Ser Ser Gly Glu Ile Arg Thr Leu His Pro Phe Trp Glu Asp Val Thr
                645                 650                 655

Pro Val Val Glu Leu Val Lys Val Thr Asp His Gly Lys Pro Thr
            660                 665                 670

Leu Ser Ala Val Ala Lys Leu Ile Ile Arg Ser Val Ser Gly Ser Leu
            675                 680                 685

Pro Glu Gly Val Pro Arg Val Asn Gly Glu Gln His His Trp Asp Met
690                 695                 700

Ser Leu Pro Leu Ile Val Thr Leu Ser Thr Ile Ser Ile Ile Leu Leu
705                 710                 715                 720

Ala Ala Met Ile Thr Ile Ala Val Lys Cys Lys Arg Glu Asn Lys Glu
                725                 730                 735

Ile Arg Thr Tyr Asn Cys Arg Ile Ala Glu Tyr Ser His Pro Gln Leu
                740                 745                 750

Gly Gly Gly Lys Gly Lys Lys Lys Ile Asn Lys Asn Asp Ile Met
            755                 760                 765

Leu Val Gln Ser Glu Val Glu Glu Arg Asn Ala Met Asn Val Met Asn
770                 775                 780

Val Val Ser Ser Pro Ser Leu Ala Thr Ser Pro Met Tyr Phe Asp Tyr
785                 790                 795                 800

Gln Thr Arg Leu Pro Leu Ser Ser Pro Arg Ser Glu Val Met Tyr Leu
                805                 810                 815

Lys Pro Ala Ser Asn Asn Leu Thr Val Pro Gln Gly His Ala Gly Cys
            820                 825                 830

His Thr Ser Phe Thr Gly Gln Gly Thr Asn Ala Ser Glu Thr Pro Ala
            835                 840                 845

Thr Arg Met Ser Ile Ile Gln Thr Asp Asn Phe Pro Ala Glu Pro Asn
850                 855                 860

Tyr Met Gly Ser Arg Gln Gln Phe Val Gln Ser Ser Thr Phe Lys
865                 870                 875                 880

Asp Pro Glu Arg Ala Ser Leu Arg Asp Ser Gly His Gly Asp Ser Asp
                885                 890                 895

Gln Ala Asp Ser Asp Gln Asp Thr Asn Lys Gly Ser Cys Cys Asp Met
            900                 905                 910

Ser Val Arg Glu Ala Leu Lys Met Lys Thr Thr Ser Thr Lys Ser Gln
            915                 920                 925

Pro Leu Glu Gln Glu Pro Glu Glu Cys Val Asn Cys Thr Asp Glu Cys
930                 935                 940

Arg Val Leu Gly His Ser Asp Arg Cys Trp Met Pro Gln Phe Pro Ala
945                 950                 955                 960

Ala Asn Gln Ala Glu Asn Ala Asp Tyr Arg Thr Asn Leu Phe Val Pro
                965                 970                 975

Thr Val Glu Ala Asn Val Glu Thr Glu Thr Tyr Glu Thr Val Asn Pro
            980                 985                 990

Thr Gly Lys Lys Thr Phe Cys Thr Phe Gly Lys Asp Lys Arg Glu His
            995                1000                1005

Thr Ile Leu Ile Ala Asn Val Lys Pro Tyr Leu Lys Ala Lys Arg Ala
```

```
                1010                1015                1020
Leu Ser Pro Leu Leu Gln Glu Val Pro Ser Ala Ser Ser Pro Thr
1025                1030                1035                1040

Lys Ala Cys Ile Glu Pro Cys Thr Ser Thr Lys Gly Ser Leu Asp Gly
                1045                1050                1055

Cys Glu Ala Lys Pro Gly Ala Leu Ala Glu Ala Ser Ser Gln Tyr Leu
                1060                1065                1070

Pro Thr Asp Ser Gln Tyr Leu Ser Pro Ser Lys Gln Pro Arg Asp Pro
        1075                1080                1085

Pro Phe Met Ala Ser Asp Gln Met Ala Arg Val Phe Ala Asp Val His
    1090                1095                1100

Ser Arg Ala Ser Arg Asp Ser Ser Glu Met Gly Ala Val Leu Glu Gln
1105                1110                1115                1120

Leu Asp His Pro Asn Arg Asp Leu Gly Arg Glu Ser Val Asp Ala Glu
                1125                1130                1135

Glu Val Val Arg Glu Ile Asp Lys Leu Leu Gln Asp Cys Arg Gly Asn
                1140                1145                1150

Asp Pro Val Ala Val Arg Lys
        1155

<210> SEQ ID NO 18
<211> LENGTH: 25
<212> TYPE: RNA
<213> ORGANISM: Artificial Sequence
<220> FEATURE:
<223> OTHER INFORMATION: Si-RNA for CDH6

<400> SEQUENCE: 18
uuucauagaa cucagcaaau ucugg                                                25

<210> SEQ ID NO 19
<211> LENGTH: 25
<212> TYPE: RNA
<213> ORGANISM: Artificial Sequence
<220> FEATURE:
<223> OTHER INFORMATION: Si-RNA for CDH6

<400> SEQUENCE: 19
uaauaaugaa gagaucuccu gcucc                                                25
```

METHOD FOR SCREENING AN AGENT PREVENTING OR TREATING CANCER USING GLYCYL-TRNA SYNTHETASE AND CADHERIN

CROSS REFERENCE TO RELATED APPLICATIONS

This application is the continuation of International Application PCT/KR2012/008211, filed on Oct. 10, 2012, and claims priority from and the benefit of Korean Patent Application No. 10-2011-0103306 filed on Oct. 10, 2011, both of which are incorporated herein by reference in their entireties for all purposes as if fully set forth herein.

BACKGROUND

1. Field

The present invention relates to a novel method of screening an agent for preventing or treating cancer using glycyl-tRNA synthetase (GRS) and cadherin. More is particularly, it relates to a method of screening a test agent which modulates the binding level of GRS or their fragment with CDH.

2. Discussion of the Background

As ancient proteins that arose as part of the development of the genetic code, aminoacyl tRNA synthetases (AARSs) are essential components of the translation apparatus. The 20 enzymes, one for each amino acid, catalyze the attachment of each amino acid to its cognate tRNA in the cytoplasm, where the charged tRNAs are then used for ribosomal protein synthesis. Surprisingly, ex-translational functions have been discovered for many tRNA synthetases, including gene regulation in *E. coli*, RNA splicing in mitochondria of *N. crassa*, (Kemper et al., 1992. Mol. Cell. Biol. 12, 499-511) and a diverse variety of functions in vertebrates that include among others regulation of inflammatory responses and of angiogenesis (Park et al., 2005. Trends. Biochem. Sci. 30, 569-574). These expanded functions are associated with the accretive additions of specialized motifs and domains such as internal short sequence motifs and appended GST, leucine zipper, and helix-turn-helix domains (Guo et al., 2010. FEBS Lett. 584, 434-442). The specialized motif and domain additions facilitate new protein-protein interactions that confer novel functions. Some of the many disease connections to AARSs, and to proteins that are part of the multi-tRNA synthetase complex in mammalian cells, is thought to result from disruptions to, or alterations of, their ex-translational functions (Park et al., 2008; Sampath et al., 2004). Indeed, there are dominant Charcot-Marie-Tooth disease-causing mutations in tyrosyl- and glycyl-tRNA synthetases that do not disrupt aminoacylation activity (Jordanova et al., 2006. Nat. Genet. 38, 197-202; Nangle et al., 2007. Proc. Natl. Acad. Sci. USA 104, 11239-11244).

Also surprising for essential components of the translation apparatus was the observation that specific fragments (produced by alternative splicing or natural proteolysis) of tyrosyl- and tryptophanyl-tRNA synthetases (YRS and WRS) bind to and signal through extracellular receptors, including CXCR1 and 2 on PMN cells (YRS) (Wakasugi and Schimmel, 1999. Science 284, 147-151) and VE-cadherin on endothelial cells (WRS). These two synthetases are secreted from mammalian cells under specific conditions that potentiate their ex-translational functions (Wakasugi et al., 2002. Proc. Natl. Acad. Sci. USA 99, 173-177; Yang et al., 2007. Structure 15, 793-805). Collectively, these observations raised the possibility that one way to discover ex-translational functions of tRNA synthetases might be by annotating those that were present in a physiological setting that did not carry out translation (Park et al., 2008, Proc. Natl. Acad. Sci. USA 105, 11043-11049; Sampath et al., 2004. Cell 119, 195-208). This consideration led us to examine the presence of specific synthetases in human serum.

SUMMARY

In part because of our ongoing investigations of its structure-function relationships of AARS and clinical observations, we focused on GRS. These observations led us to attempt to understand a potential role for GRS as a circulating protein in cancer microenvironments thereby completing the present invention by confirming that CDH acts as a receptor for GRS and modulates ERK pathway and regulates death and growth of cells.

Accordingly, an object of the present invention is to provide a method of screening an agent for preventing or treating cancer comprising:

(a) measuring a first binding affinity between GRS (glycyl-tRNA synthetase) or a GRS fragment and CDH (cadherin);

(b) measuring second binding affinities between the GRS or the fragment, and CDH (cadherin), in the presence of test agents;

(c) comparing the first binding affinity to each of the second binding affinities; and (d) identifying the test agents that change the binding affinity between the GRS or fragment, and the CDH, by using the result of the comparison.

According to another aspect of the present disclosure, the method may further include measuring apoptosis of CDH expressing cells in the presence of each of the identified test agents.

Accordingly, the present invention relates to a novel use of GRS and CDH and provides a method of screening an agent for preventing or treating cancer. The method may be used for developing novel agent for treatment of various cancers.

BRIEF DESCRIPTION OF THE DRAWINGS

The above and other aspects, features and advantages of the present invention will be more clearly understood from the following detailed description taken in conjunction with the accompanying drawings, in which.

DETAILED DESCRIPTION OF THE ILLUSTRATED EMBODIMENTS

Figure 1:
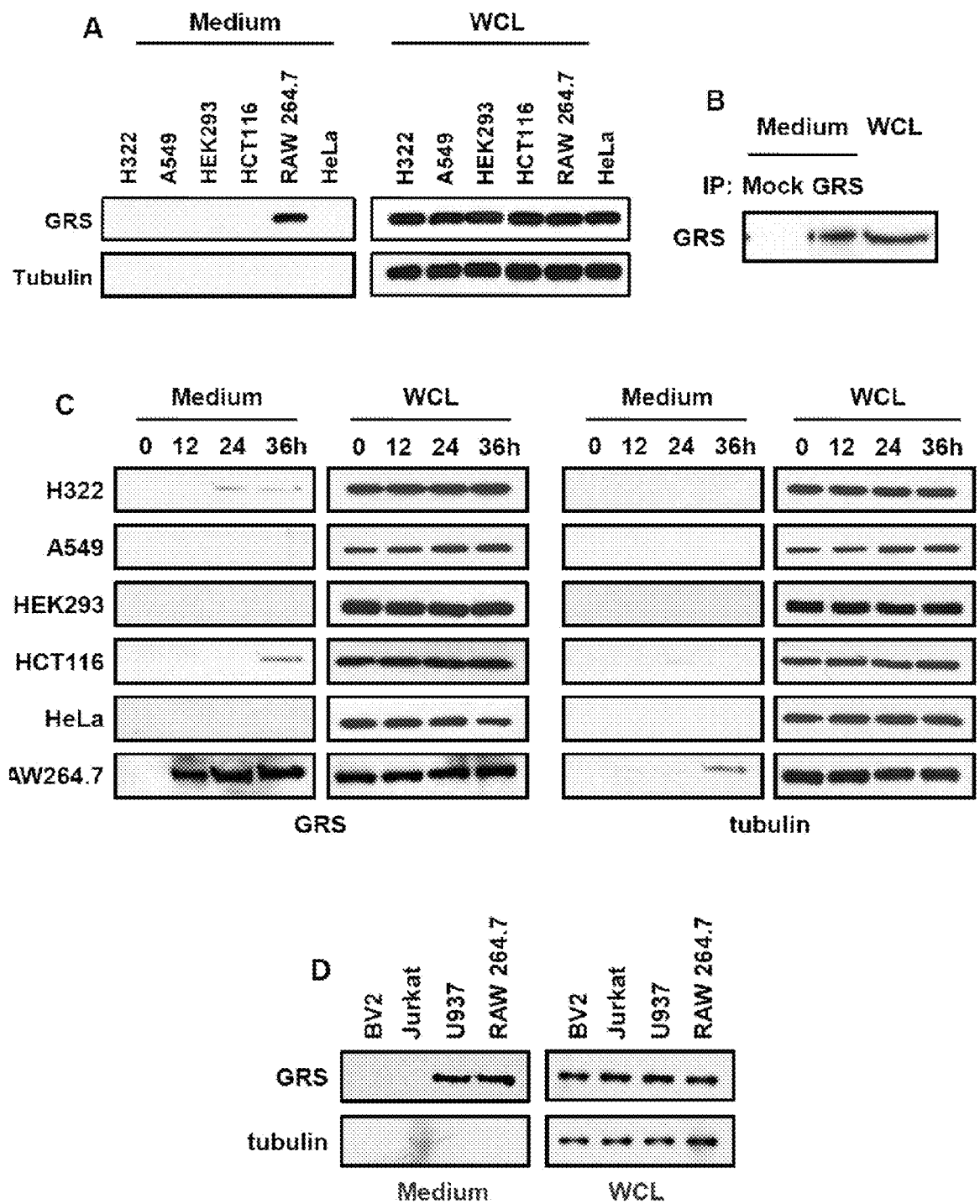
FIG. 1 shows that GRS is secreted from macrophages.

Hereinafter, a preferred embodiment of the present invention will be described with reference to the accompanying drawings.

Hereinafter, the present invention will be described in more detail.

DEFINITION

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY. In addition, the following definitions are provided to assist the reader in the practice of the invention.

An "expression", as used herein, refers to formation of protein or nucleic acid in cells.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and/or the like.

The term "polypeptide" is used interchangeably herein with the terms "polypeptides" and "protein(s)", and refers to a polymer of amino acid residues, e.g., as typically found in proteins in nature.

The term "GRS polypeptide," refers to a polypeptide known as glycyl tRNA synthetase. The said GRS polypeptide may be a polypeptide having an amino acid sequence of SEQ ID NO: 1 (GenBank Accession No: AAA86443.1) or GenBank Accession No AAA57001.1 (SEQ ID NO:5), EAL24449.1 (SEQ ID NO:6), BAA06338.1 (SEQ ID NO:7), NP_002038.2 (SEQ ID NO:8), AAH07755.1 (SEQ ID NO:9), AAH07722.1 (SEQ ID NO:10). And the GRS comprises functional equivalents thereof.

The term "GRS fragment" refers to a fraction of Full length GRS polypeptide and it comprises an anticodon binding domain of C-terminal. For example, it may be a fragment which consists of amino acids from the 511th to the last 685th amino acid (SEQ ID NO:2) of full length GRS amino acid of SEQ ID NO: 1 and comprises an anticodon binding domain of C-terminal (SEQ ID NO: 11, from 511th to 674th amino acid of SEQ ID NO:1). In addition, the GRS fragment comprises a functional equivalent thereof. Meanwhile, a mitochondrial form of GRS (for example, SEQ ID NO: 7) differ from cytosol form (for example, SEQ ID NO: 1) in that 54 amino acid were added. Therefore, the location of a binding domain of C-terminal could be considered by the skilled person in the art reflecting the point.

The term "functional equivalents" refers to polypeptide comprising the amino acid sequence having at least 70% amino acid sequence homology (i.e., identity), preferably at least 80%, and more preferably at least 90%, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% amino acid sequence homology, that exhibit substantially identical physiological activity to the amino acid sequence of GRS or a fragment thereof and it refers to polypeptide having substantially identical physiological activity with polypeptide represented by SEQ ID NO: 1 or SEQ ID NO: 2. The "substantially identical physiological activity" means inhibition or death of cancer cell by activating ERK pathway by binding CDH, more particularly CDH6 or CDH18. The functional equivalents may include, for example peptides produced by as a result of addition, substitution or deletion of some amino acid of SEQ ID NO:1. Substitutions of the amino acids are preferably conservative substitutions. Examples of conservative substitutions of naturally occurring amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). Furthermore, the functional equivalents also include variants with deletion of some of the amino acid sequence of the GRS of the present invention. Deletion or substitutions of the amino acids are preferably located at regions that are not directly involved in the physiological activity of the inventive polypeptide. And deletion of the amino acids is preferably located at regions that are not directly involved in the physiological activity of the GRS. In addition, the functional equivalents also include variants with addition of several amino acids in both terminal ends of the amino acid sequence of the GRS or in the sequence. Moreover, the inventive functional equivalents also include polypeptide derivatives which have modification of some of the chemical structure of the inventive polypeptide while maintaining the fundamental backbone and physiological activity of the inventive polypeptide. Examples of this modification include structural modifications for changing the stability, storage, volatility or solubility of the inventive polypeptide.

Sequence identity or homology is defined herein as the percentage of amino acid residues in the candidate sequence that are identical with amino acid sequence of GRS (SEQ ID NO: 1), after aligning the sequences and introducing gaps, if necessary, to achieve the maximum percent sequence identity, and not considering any conservative substitutions (as described above) as part of the sequence identity. None of N-terminal, C-terminal, or internal extensions, deletions, or insertions into the amino acid sequence of GRS shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a predetermined portion of one or both sequences). The programs provide a default opening penalty and a default gap penalty, and a scoring matrix such as PAM 250 (a standard scoring matrix; see Dayhoff et al., in Atlas of Protein Sequence and Structure, vol. 5, supp. 3 (1978)) can be used in conjunction with the computer program. For example, the percent identity can be calculated as the follow. The total number of identical matches multiplied by 100 and then divided by the sum of the length of the longer sequence within the matched span and the number of gaps introduced into the longer sequences in order to align the two sequences.

The polypeptide according to the present invention can be prepared by separating from nature materials or genetic engineering methods. For example, a DNA molecule encoding the polypeptide or its functional equivalents (ex: In case of GRS, SEQ ID NO: 3, and in case of fragment of GRS, SEQ ID NO: 4) is constructed according to any conventional method. The DNA molecule may synthesize by performing PCR using suitable primers. Alternatively, the DNA molecule may also be synthesized by a standard method known in the art, for example using an automatic DNA synthesizer (commercially available from Biosearch or Applied Biosystems). The constructed DNA molecule is inserted into a vector comprising at least one expression control sequence (ex: promoter, enhancer) that is operatively linked to the DNA sequence so as to control the expression of the DNA molecule, and host cells are transformed with the resulting recombinant expression vector. The transformed cells are cultured in a medium and condition suitable to express the DNA sequence, and a substantially pure polypeptide encoded by the DNA sequence is collected from the culture medium. The collection of the pure polypeptide may be performed using a method known in the art, for example, chromatography. In this regard, the term "substantially pure polypeptide" means the inventive polypeptide that does not substantially contain any other proteins derived from host cells. For the genetic engineering method for synthesizing the inventive polypeptide, the reader may refer to the following literatures: Maniatis et al., *Molecular Cloning: A Laboratory Manual*, Cold Spring Harbor Laboratory 1982; Sambrook et al., *Molecular Cloning; A Laboratory Manual*, Cold Spring Harbor Press, N.Y., Second (1998) and Third (2000) Editions; *Gene Expression Technology, Method in Enzymology, Genetics and Molecular Biology, Method in Enzymology*, Guthrie & Fink (eds.), Academic Press, San Diego, Calif. 1991; and Hitzeman et al., *J. Biol. Chem.*, 255, 12073-12080 1990.

Alternatively, the inventive polypeptide can be chemically synthesized easily is according to any technique known in the art (Creighton, Proteins: Structures and Molecular Principles, W.H. Freeman and Co., NY, 1983). As a typical technique, they are not limited to, but include liquid or solid phase synthesis, fragment condensation, F-MOC or T-BOC chemistry (Chemical Approaches to the Synthesis of Peptides and Proteins, Williams et al., Eds., CRC Press, Boca Raton Fla., 1997; A Practical Approach, Atherton & Sheppard, Eds., IRL Press, Oxford, England, 1989).

The terms "nucleic acid," "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides.

The "promoter" means a DNA sequence regulating the expression of nucleic acid sequence operably linked to the promoter in a specific host cell, and the term "operably linked" means that one nucleic acid fragment is linked to other nucleic acid fragment so that the function or expression thereof is affected by the other nucleic acid fragment. Additionally, the promoter may include an operator sequence for controlling transcription, a sequence encoding a suitable mRNA ribosome-binding site, and sequences controlling the termination, transcription and translation. Additionally, it may be constitutive promoter which constitutively induces the expression of a target gene, or inducible promoter which induces the expression of a target gene at a specific site and a specific time.

The term "the nucleotide encoding GRS" may have a nucleic acid encoding a polypeptide having the amino acid sequence of SEQ ID NO: 1 or a polypeptide having the amino acid sequence homology of at least 70% to the polypeptide. The nucleic acid includes DNA, cDNA or RNA. The polynucleotide may have a nucleotide sequence encoding the amino acid sequence of SEQ ID NO: 1 or an amino acid sequence homology of at least 70% to SEQ ID NO: 1. Preferably, the polynucleotide comprises the nucleotide sequence of SEQ ID NO. 3. The nucleic acid can be isolated from a natural source or be prepared by a genetic engineering method known in the art.

Further, the nucleotide encoding GRS fragment may have a nucleic acid encoding a polypeptide having the amino acid sequence of SEQ ID NO: 1 or a polypeptide having the amino acid sequence homology of at least 70% to the polypeptide. Preferably, the polynucleotide comprises the nucleotide sequence of SEQ ID NO. 4. The nucleic acid can be isolated from a natural source or be prepared by a genetic engineering method known in the art.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

The term "homologous" when referring to proteins and/or protein sequences indicates that they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence.

As used herein, "contacting" has its normal meaning and refers to combining two or more agents (e.g., two polypeptides) or combining agents and cells (e.g., a protein and a cell). Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

More specifically, test agents that can be identified with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test agents are synthetic molecules, and others natural molecules. Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, or "biased" random peptides.

The test agents can also be "nucleic acids". Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. A number of assays are available for such screening, e.g., as described in Schultz (1998) Bioorg Med Chem Lett 8:2409-2414; The present inventors (1997) Mol. Divers. 3:61-70; Fernandes (1998) Curr Opin Chem Biol 2:597-603; and Sittampalam (1997) Curr Opin Chem Biol 1:384-91.

The library of the test agents for the screening method of the present invention can be prepared through structure studies about GRS, its fragment or its analogue. The test agents which can bind to GRS may be identified by such structure studies.

The three-dimensional structures of GRS can be studied in a number of ways, is e.g., crystal structure and molecular modeling. Methods of studying protein structures using x-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Computer modeling of structures of GRS provides another means for designing test agents for screening GRS. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interrscience, New York 1986).

The present inventors investigated that GRS (glycyl tRNA synthetase) interacts with CDH and regulates ERK pathway thereby modulating death and growth of cells. That is, the present inventors confirmed that GRS interacts with CDH6 and regulates ERK pathway through PP2A thereby modulating death and growth of cells.

Accordingly, the present invention provides a method of screening an agent for preventing or treating cancer comprising:
(a) contacting GRS (glycyl-tRNA synthetase) or its fragment, CDH (cadherin) and with or without a test agent;
(b) measuring a binding affinity between GRS or its fragment, and CDH with or without a test agent;
(c) comparing the binding affinity between GRS or its fragment, and CDH with a test agent to the binding affinity between GRS or its fragment, and CDH without a test agent; and
(d) identifying the test agent which changes the binding affinity between GRS or its fragment, and CDH.

More particularly, the cancer comprises, but are not limited to, malignant melanoma, leukaemia, colon cancer, lung cancer, liver cancer, stomach cancer, esophagus cancer, pancreatic cancer, gall bladder cancer, kidney cancer, bladder cancer, prostate cancer, testis cancer, cervical cancer, endometrial carcinoma, choriocarcinoma, ovarian cancer, breast cancer, thyroid cancer, brain tumor, head or neck cancer, skin cancer, lymphoma, and it also comprises B-cell neoplasms such as precursor B-cell neoplasm, T-cell and NK-cell neoplasm such as precursor T-cell neoplasm and Hodgkin lymphoma (Hodgkin disease) such as Classical Hodgkin lymphoma.

In addition, a protein interacting GRS or a fragment thereof may be CDH (cadherin) and preferably, it may be CDH6 (K-cadherin, cadherin-6) or CDH18 (cadherin-18). The CDH6 or CDH18 may be a sequence disclosed in Genbank. More preferably, in case of CDH6, it may be SEQ ID NO: 12 (Genbank Accession No. AAH00019.1), SEQ ID NO: 13 (Genbank Accession NO. NP_004923.1) or SEQ ID NO: 14 (Genbank Accession No. BAA06562.1). In case of CDH18, it may be SEQ ID NO: 15 (Genbank Accession No. AAH31051.1), SEQ ID NO: 16 (Genbank Accession No. EAW68851.1) or SEQ ID NO: 17 (Genbank Accession No. NP_001035519.1). In the example of the present invention, SEQ ID NOs. 12 and 15 were used for CDH6 and CDH18.

Meanwhile, the screening method may use a GRS fragment interacting CDH6. By using a fragment comprising a anticodon binding domain of a GRS fragment, for example, a fragment represented by SEQ ID NO: 2, the present invention provides a method of screening an agent for preventing or treating cancer comprising:
(a) measuring a first binding affinity between GRS (glycyl-tRNA synthetase) or a GRS fragment and CDH (cadherin);
(b) measuring second binding affinities between the GRS or the fragment, and CDH (cadherin), in the presence of test agents;
(c) comparing the first binding affinity to each of the second binding affinities; and
(d) identifying the test agents that change the binding affinity between the GRS or fragment, and the CDH, by using the result of the comparison.

Meanwhile, in some embodiments, the screening method further comprises measuring apoptosis of CDH expressing cells in the presence of each of the identified test agents.

In the present invention, since GRS or its fragment induces death of cancer cells by interacting CDH through ERK pathway, a test agent which changes binding level of the GRS or its fragment and CDH interacts with CDH and it could induce apoptosis of CDH expressing cells. The test agent may mimic GRS for binding to CDH. Preferably, the test agent that changes the binding affinity between GRS or its fragment, and CDH, may be an inhibitor for binding between GRS or its fragment, and CDH.

In the present invention, a CDH expressing cell may be a CDH6 or CDH18 expressing cell and preferably, it may be a cancer cell, and more preferably, it may be a kidney cancer cell, a liver cancer cell, a lung cancer cell, a colon cancer cell or originated/differentiated cells from thereof.

In the present invention, change of binding level of the GRS and CDH may be increase of decrease. For example, increase of change of binding level of the GRS and CDH may stimulate (or increase) death of cells through inducing signal transduction to ERK and decrease of change of binding level of the GRS and CDH may stimulate (or increase) cell death through mimicking function of GRS.

Various biochemical and molecular biology techniques or assays well known in the art can be employed to practice the present invention. Such techniques are described in, e.g., Sambrook et al., Molecular Cloning: A Laboratory Manual, Cold Spring Harbor Press, N.Y., Second (1989) and Third (2000) Editions; and Ausubel et al., Current Protocols in Molecular Biology, John Wiley & Sons, Inc., New York (1987-1999).

Preferably, the test agent is first assayed for their ability to modulate a biological activity of GRS or CDH (the first assay step). Particularly, in the first step, modulating agents that modulate a biological activity of the polypeptide may be identified by assaying a biological activity of isolated GRS in the presence of a test agent. More preferably, the present invention may comprise:

(a) contacting test agents with GRS or CDH in the presence of a test agent; and
(b) measuring activity of GRS or CDH and selecting a testing agent which changes activity of GRS or CDH.

Modulation of different biological activities of GRS or CDH can be assayed in the first step. For example, a test agent can be assayed for activity to modulate expression level of GRS or CDH, e.g., transcription or translation. The test agent can also be assayed for activities in modulating cellular level or stability of GRS or CDH, e.g., post-translational modification or proteolysis.

Test agents that increase a biological activity by the first assay step are identified. The test agents are then subject to further testing to determine whether the test agents have ability to change the interaction of the GRS and CDH (the second testing step).

In both the first step and the second step, an intact GRS and subunits or their fragments, analogs, or functional derivatives can be used. The fragments that can be employed in these assays usually retain one or more of the biological activities of GRS. And fusion proteins containing such fragments or analogs can also be used for the screening of test agents. Functional derivatives of GRS usually have amino acid deletions and/or insertions and/or substitutions while maintaining one or more of the bioactivities and therefore can also be used in practicing the screening methods of the present invention.

A variety of the well-known techniques can be used to identify test agents that modulate GRS or CDH. Preferably, the test agents are screened with a cell based assay system. For example, in a typical cell based assay (i.e., the second screening step), activity of the reporter gene (i.e., enzyme activity) is measured in the presence of test agent, and then compared the activity of the reporter gene in the absence of test agent. The reporter gene can encode any detectable polypeptide (response or reporter polypeptide) known in the art, e.g., detectable by fluorescence or phosphorescence or by virtue of its enzymatic activity. The detectable response polypeptide can be, e.g., luciferase, alpha-glucuronidase, alpha-galactosidase, chloramphenicol acetyl transferase, green fluorescent protein, enhanced green fluorescent protein, and the human secreted alkaline phosphatase.

In the cell-based assays, the test agent (e.g., a peptide or a polypeptide) can also be expressed from a different vector that is also present in the host cell. In some methods, a library of test agents is encoded by a library of such vectors (e.g., a cDNA library; see the Example below). Such libraries can be generated using methods well known in the art (see, e.g., Sambrook et al. and Ausubel et al., supra) or obtained from a variety of commercial sources.

In addition to cell based assays described above, it can also be screened with non-cell based methods. These methods include, e.g., mobility shift DNA-binding assays, methylation and uracil interference assays, DNase and hydroxy radical footprinting analysis, fluorescence polarization, and UV crosslinking or chemical cross-linkers. For a general overview, see, e.g., Ausubel et al., supra (chapter 12, DNA-Protein Interactions). One technique for isolating co-associating proteins, including nucleic acid and DNA/RNA binding proteins, includes use of UV crosslinking or chemical cross-linkers, including e.g., cleavable cross-linkers dithiobis(succinimidylpropionate) and 3,3'-dithiobis(sulfosuccinimidyl-propionate); see, e.g., McLaughlin, Am. J. Hum. Genet., 59:561-569, 1996; Tang, Biochemistry, 35:8216-8225, 1996; Lingner, Proc. Natl. Acad. Sci. U.S.A., 93:10712, 1996; and Chodosh, Mol. Cell. Biol., 6:4723-4733, 1986.

Hereafter, the figures of the present invention will be described.

FIG. 1 shows that GRS is secreted from macrophages. (A) The indicated cells were incubated in serum-free medium for 12 h and the proteins secreted to the culture media were precipitated with TCA and subjected to immunoblotting with anti-GRS antibodies (Medium). Expression levels of GRS were determined by immunoblotting of GRS in whole cell lysates (WCL). (B) RAW 264.7 cells were incubated in serum-free medium for 12 h and the proteins in the culture medium were immunoprecipitated and immunoblotted with anti-GRS antibodies. (C) The time course of GRS secretion from different cell types in serum-free medium was monitored at the indicated times. (D) The secretion of GRS from microglia (BV2), T lymphocyte (Jurkat), and macrophage-like monocytic cells (U937) was determined in serum-free medium for 12 h as described above.

Figure 2:
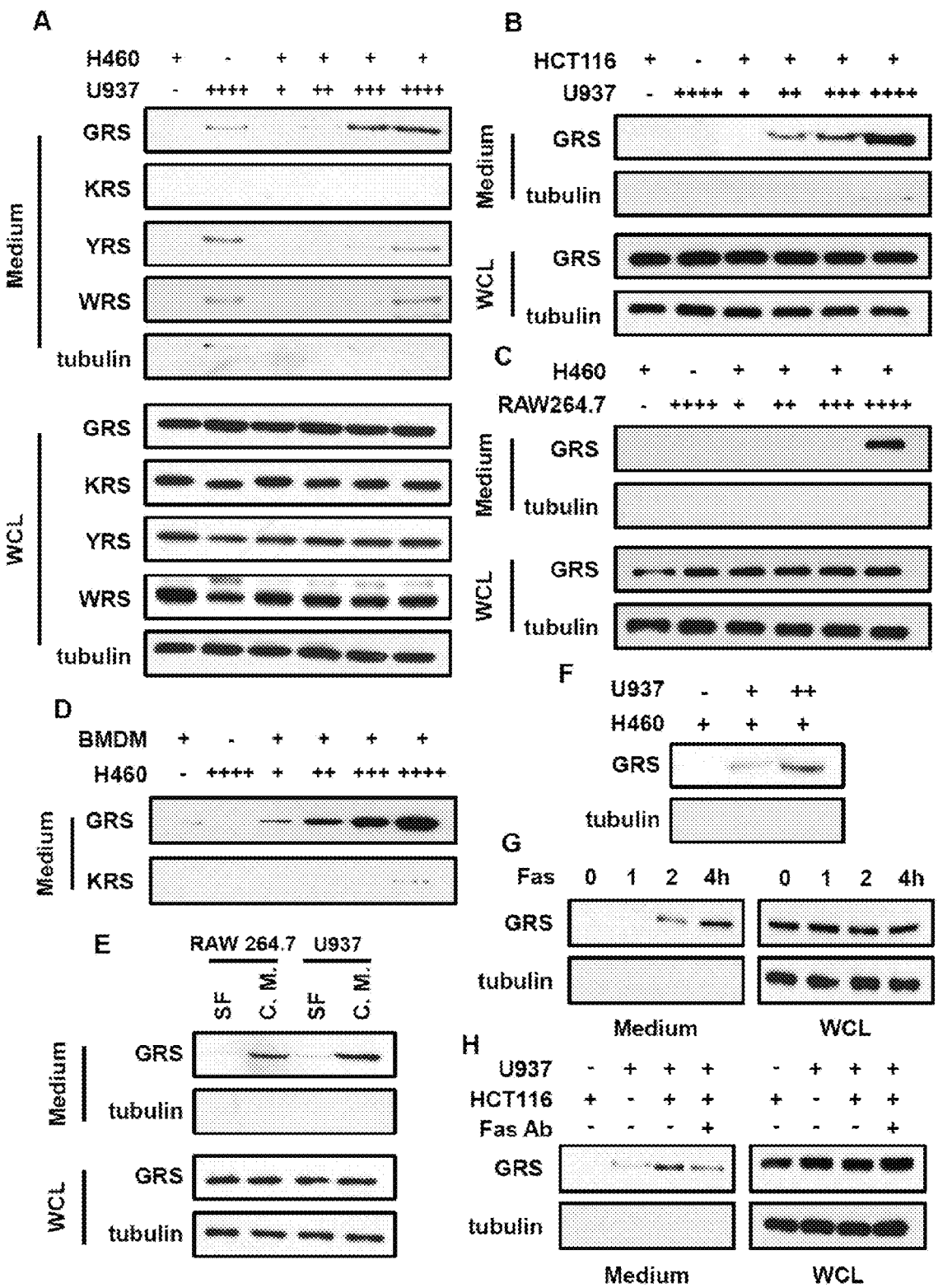
FIG. 2 shows that GRS secretion can be induced by a Fas ligand signal derived from cancer cells.

FIG. 2 shows that GRS secretion can be induced by a Fas ligand signal derived is from cancer cells. (A) H460 cancer cells were first seeded ($0.25 \times 10^6$ cells/well). After 12 h, the medium was changed with serum-free medium and the cells were co-cultured with U937 monocytes ($0.125 \times 10^6 \sim 1 \times 10^6$ cells/well) for 6 h. Then, secretion of GRS in the cultured medium was determined by TCA precipitation and immunoblotting. (B) Co-cultivation of HCT116 cancer cells with U937 cells and determination of GRS secretion were determined as stated above. (C) H460 and RAW 264.7 cells were co-cultured and the secretion of GRS was determined. (D) Bone marrow-derived macrophage (BMDM) and H460 cells were co-incubated and GRS secretion was monitored. (E) The cultured medium of H460 cells was harvested after 12 h incubation, and used as the conditioned medium (CM) for RAW 264.7 and U937 cells for 6 h. The secretion of GRS was determined as above. (F) H460 cells were incubated in a Transwell chamber with or without U937 cells in the insert for 6 h in serum-free medium and the secretion of GRS was analyzed. (G) U937 cells were treated with activating anti-Fas antibody (CH11 clone, 5 mg/ml) at the indicated times and the secretion of GRS was determined. (H) Neutralizing anti- Fas antibody (ZB4 clone, 0.2 ug/ml) was added to the medium of the co-culture system and GRS secretion was determined as above.

Figure 3:
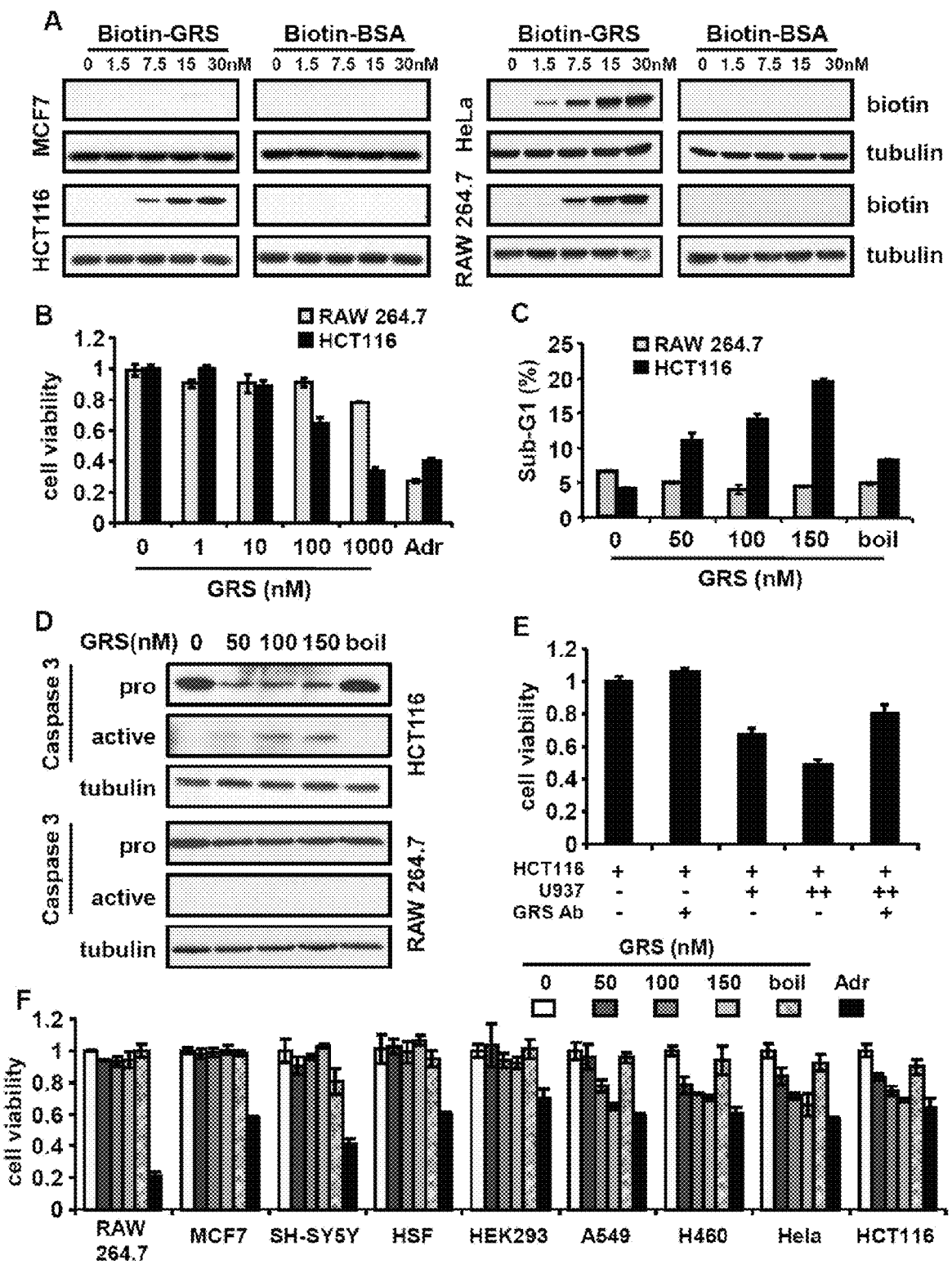
FIG. 3 shows that secreted GRS induces cell death in several different tumor cells.

FIG. 3 shows that secreted GRS induces cell death in several different tumor cells. (A) Dose-dependent binding of biotinylated GRS was determined with MCF-7, HeLa, HCT116, and RAW 264.7 cell lines by capture with streptavidin-HRP. (B) RAW 264.7 and HCT116 cells were treated with the indicated concentrations of recombinant human GRS for 24 h and the cell viability was measured by the MTT assay. Adriamycin (2 mg/ml) was used as positive control to induce cell death. (C) The effect of GRS on cell death was also monitored by sub-G1 cells using flow cytometry. The graphs indicate the percentage of sub-G1 cells. GRS (150 nM) was boiled to see whether it can inactivate the cytokine activity. (D) GRS-induced cell death was also monitored by the generation of active caspase-3. (E) Using a Transwell, U937 cells were incubated in the insert with or without HCT116 in the chamber (for 24 h) and cell viability was analyzed as above. To neutralize the effect of GRS, anti-GRS antibody was added to the culture dish. (F) RAW 264.7, MCF7, SH-SY5Y, HSF, HEK293, A549, H460, Hela and HCT116 cells were treated with the indicated concentrations of GRS or with Adriamycin for 24 h, and the effect on cell viability was determined by the MTT assay. Error bars give the mean±standard deviation from the average of 3 experiments.

Figure 4:
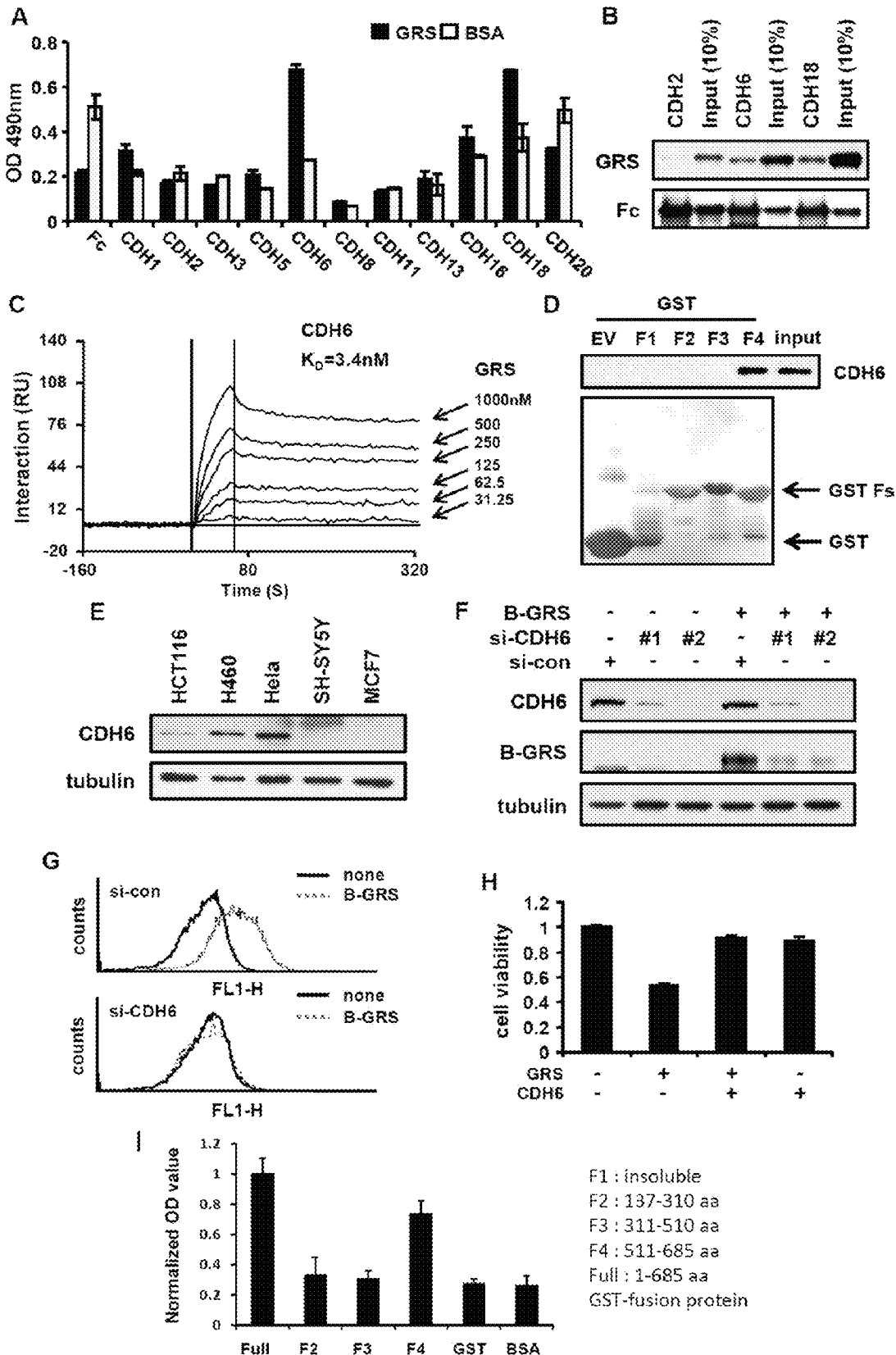
FIG. 4 shows Identification of CDH6 as a potential receptor for GRS.

FIG. 4 shows that identification of CDH6 as a potential receptor for GRS. (A) A panel of Fc-fused soluble cadherin family proteins was bound to His-tagged GRS or to BSA-coated plates, and complexes were detected with the IgG1 Fc-HRP (Thermo) reagent. (B) To confirm the binding between cadherins and GRS, Fc-CDH2, 6 and 18 were incubated with His-GRS. Fc-CDHs were precipitated with protein A/G agarose and co-precipitated GRS was determined by immunoblotting. (C) To calculate the equilibrium dissociation constant ($K_D$), immobilized Fc-fused (to gold chips) cadherins were incubated with GRS (31.25 nM~1 uM). Binding of GRS to CDH6 was determined by surface plasmon resonance and expressed as resonance units (RU). (D) To confirm the binding between CDH6 and GRS domain peptides, Fc-CDH6 was incubated with different domains (F1, 2, 3 and 4) of GRS that were expressed as the GST fusion proteins. GST-GRS proteins were precipitated with GSH-sepharose beads and co-precipitated CDH6 was determined by immunoblotting. (E) Five difference cancers cells were determined for the expression of CDH6 by immunoblotting. (F) HCT116 cells were transfected with non-specific siRNA controls (si-con) or two differently designed siRNAs targeting CDH6 (#1 and #2), treated with biotinylated GRS (15 nM), and the binding of GRS was analyzed by immunoblotting. (G) HCT116 cells were transfected with si-con and si-CDH6 as described above, and cell binding of GRS was measured by FACS analysis. (H) HCT116 cells were incubated with His-GRS (150 nM). To neutralize the effects of GRS, Fc-fused CDH6 (300 nM) was added and the cell viability was determined by the MTT assay. Error bars represent standard deviation. (I) The binding between CDH6 and GRS domain peptides was again confirmed by ELISA assay.

Figure 5:
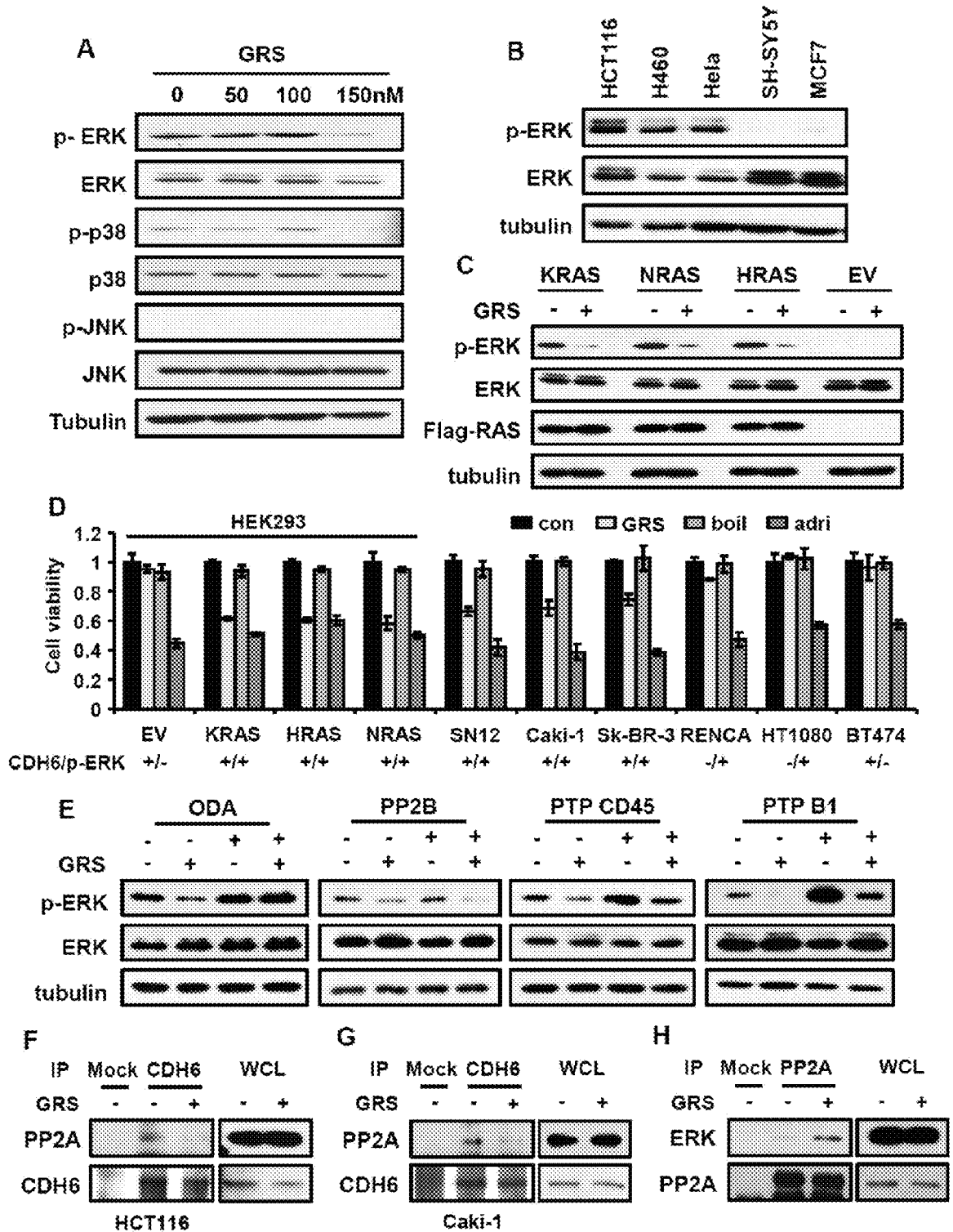
FIG. 5 shows that secreted GRS induces death of hyperphosphorylated ERK cancer cells.

FIG. 5 shows that secreted GRS induces death of hyperphosphorylated ERK cancer cells. (A) HCT116 cells were treated with the indicated concentrations of GRS for 1 h and the phosphorylation of three different MAPKs was determined by their specific antibodies. (B) Five difference cancers cell lines were investigated for the phosphorylation of ERK by immunoblotting. (C) HEK293 cells expressing each of three different active Ras transfectants were treated with GRS (150 nM) and its effect on the phosphorylation of ERK was determined as above. (D) Susceptibility of different cancer cell lines to GRS-induced cell death was determined by the MTT assay. Results shown are the mean of 3 independent experiments. (E) HCT116 cells were treated with one of okadaic acid (PP2A inhibitor), PP2B inhibitor, PTP CD45 inhibitor or PTP B1 inhibitor for 15 min and incubated in the absence or presence of GRS (150 nM) for 1 h and phosphorylation of ERK was then determined. The GRS effect on the interaction of CDH6 and PP2A was determined by co-immunoprecipitation in HCT116 (F) and Caki-1 (G) cells. (H) HCT 116 cells were treated with GRS and its effect on the interaction of PP2A and ERK was determined by co-immunoprecipitation.

Figure 6:
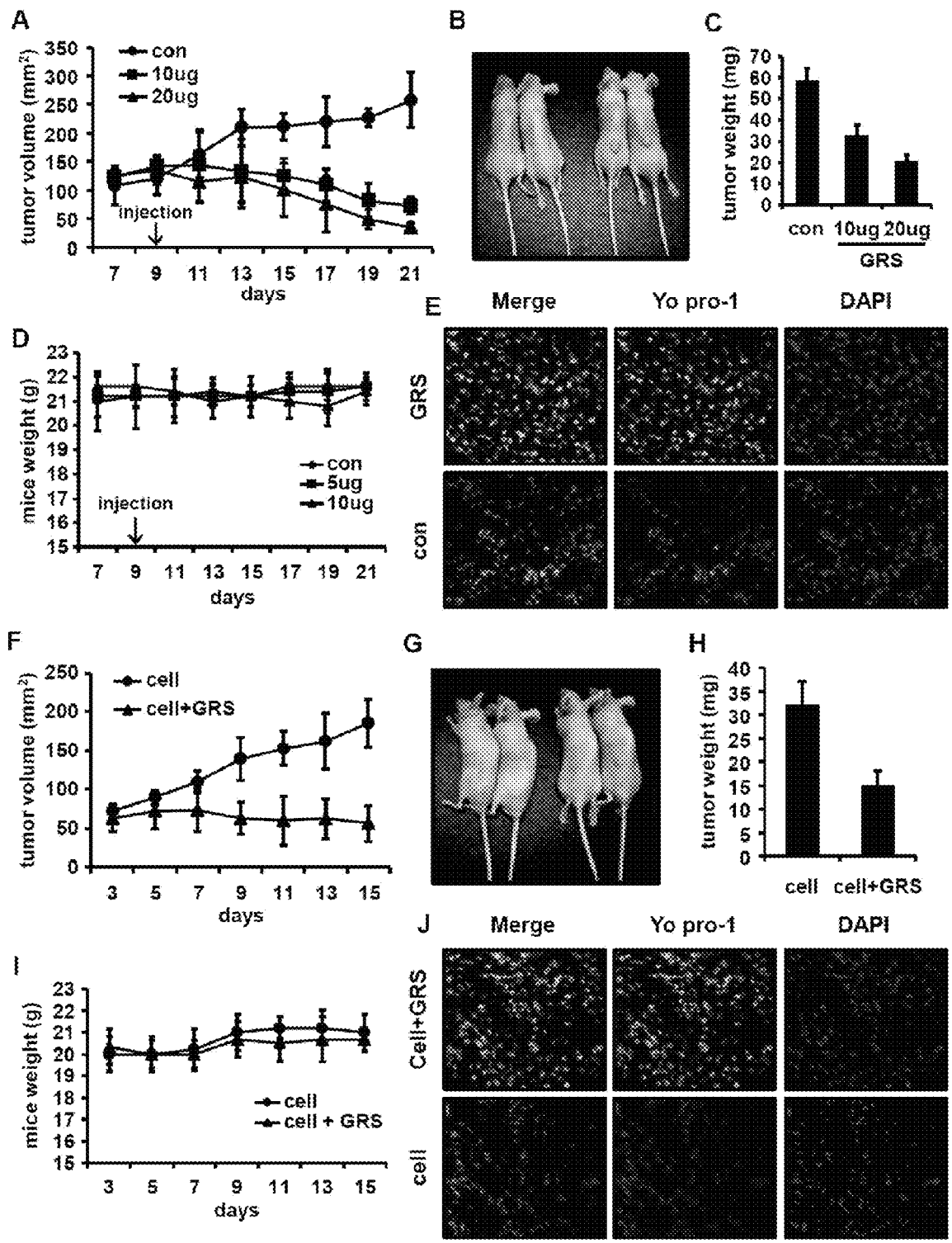
FIG. 6 shows that secreted GRS induces cancer cell death in vivo.

FIG. 6 shows that secreted GRS induces cancer cell death in vivo. (A) HCT116 cells were subcutaneously injected into the BALB/c nude mice and grown for 9 days. GRS (10 and 20 mg per dose) or PBS vehicle was intra-tumor injected (n=5 animal/group). Tumor volume was calculated as the longest diameter×the shortest diameter$^2$×0.52. (B) Photograph of two representative HCT116 xenograft tumor mice from the control (left) and treated (right, 20 mg GRS) arms 12 days after the treatment. (C) Tumor weight was measured on the same day. (D) The body weight of the control and GRS-treated groups at the indicated doses were measured. (E) The OCT compound-embedded tissues (a section of 10 mm) were used for immunofluorescence staining. The tissues were treated with Yo-pro (green) and analyzed by immunofluorescence microscopy. Nuclei were stained with DAPI (blue). (F) HCT116 cells were injected into the BALB/c nude mice as above with 20 mg GRS or PBS (n=6 animal/group), and grown for 15 days. (G) Photographs of the two representative HCT116 xenograft tumor mice from the control (left) and treated (right, 20 mg GRS) arms 15 days after injection. (H) Tumor weights of the control and treated mice were determined 15 days after injection. (I) The body weight of the control and GRS-treated (simultaneous injection of GRS and cells) groups were measured (n=5). (J) The OCT compound-embedded tissues (a section of 10 mm) were used for immunofluorescence staining.

Figure 7:
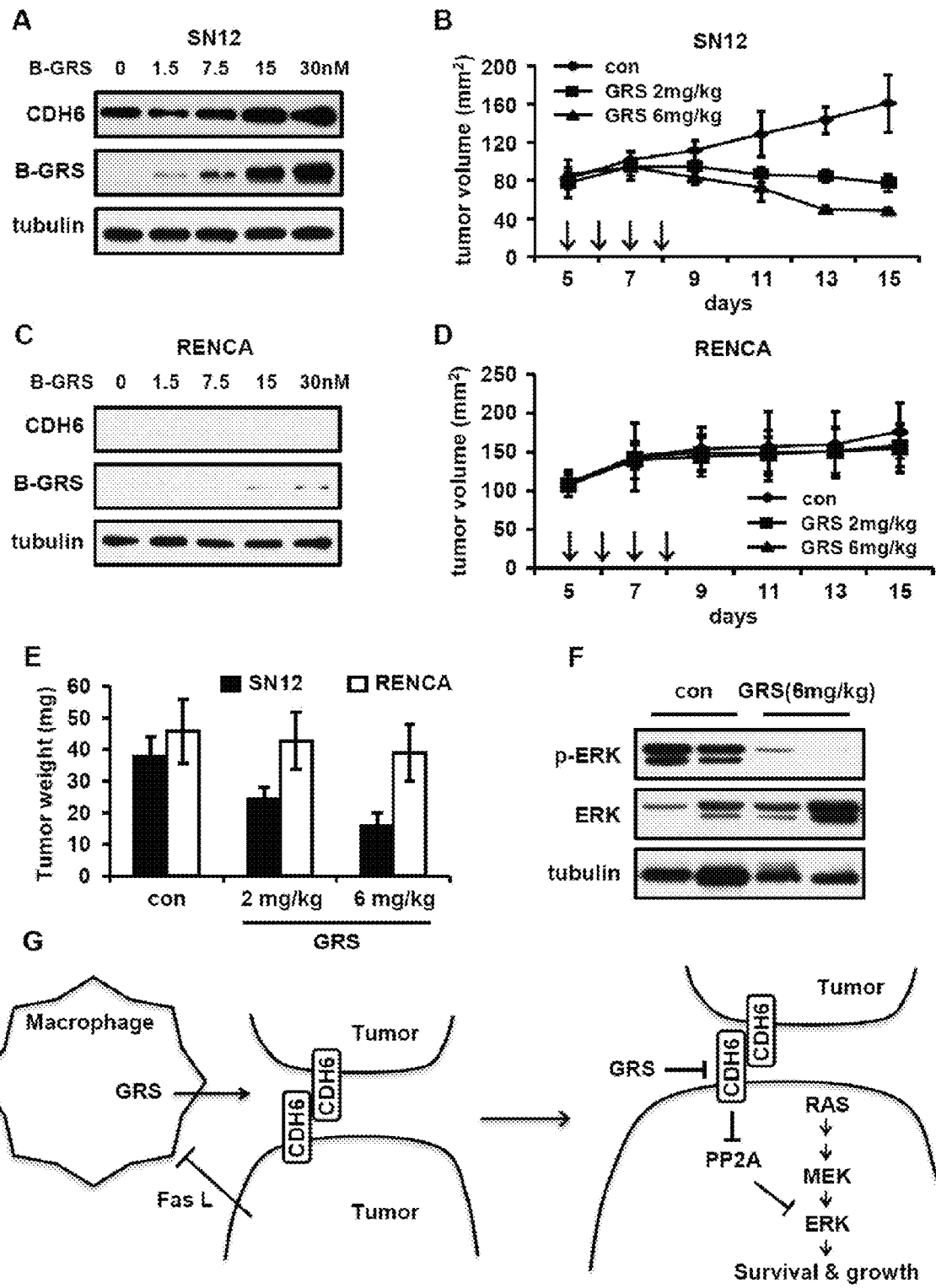
FIG. 7 shows CDH6-dependent anti-tumor effect of secreted GRS in vivo.

FIG. 7 shows CDH6-dependent anti-tumor effect of secreted GRS in vivo. (A) SN12 cells were incubated with indicated concentration of biotin-GRS (B-GRS) and the cell binding was determined by streptavidin-conjugated horseradish peroxidase. (B) SN12 cells were subcutaneously injected into the BALB/c nude mice and grown for 5 days. GRS (2 and 6 mg/kg per dose) or PBS vehicle was intra-peritoneal injected daily for 4 days (n=5 animal/group). Tumor volume was calculated as the longest diameter×the shortest diameter$^2$×0.52. (C) RENCA cells were incubated with indicated concentration of biotin-GRS and the cell binding was determined as above. (D) RENCA cells were subcutaneously injected into the BALB/c nude mice. GRS (2 and 6 mg/kg per dose) or PBS vehicle was intra-peritoneal injected as above (n=5 animal/group). Tumor volume was measured. (E) Tumor weights of the control and treated mice were determined and shown as bar graph. (F) The phosphorylation of ERK in SN12 xenograft tissues from the control and treated (6 mg/kg GRS) was determined by immunoblotting. (G) Schematic representation of the secreted GRS and its interaction with CDH6 in the tumor-macrophage microenvironment. GRS is secreted from macrophages by apoptotic stimulus like Fas ligand and binds to CDH6 that is highly expressed in the ERK-activated cancer cells, such as Ras-mutant cancer cells. Binding of GRS, releases PP2A from CDH6, leading to dephosphorylation of activated ERK, which results in target cell death.

Figure 8:
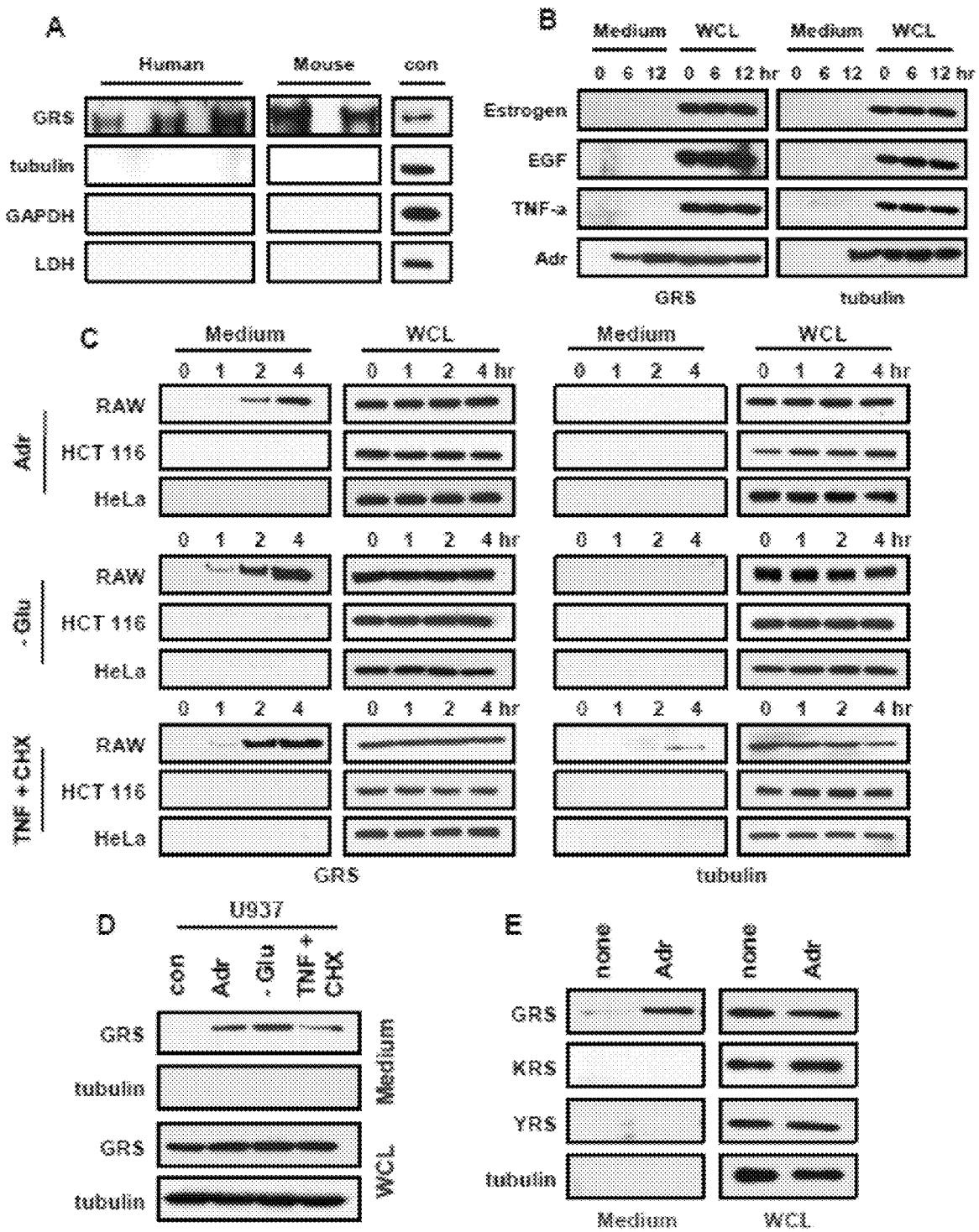
FIG. 8 shows conditions for GRS secretion.

FIG. 8 shows conditions for GRS secretion, related to FIGS. 1 and 2. (A) Detection of GRS in human and mouse serum. Serum samples (2 ml) from 3 different human subjects (approximately 80 mg of protein per sample) and from 2 different CL57BL/6 mice (approximately 40 mg of protein per sample) were resolved by SDS-PAGE and blotted with cross-reacting (human and mouse) anti-human GRS monoclonal antibodies to detect GRS. The same gels were also probed with cross-reacting (human and mouse) anti-human-beta-tubulin, -GAPDH, and -LDH monoclonal antibodies, respectively. For a positive control to check the sensitivity of the antibodies, a cell lysate (approximately 10 mg of protein) of mouse N2A cells was used. (B) RAW 264.7 cells were treated with estrogen (50 nM), EGF (100 ng/ml), TNF-a (20 ng/ml) and Adriamycin (Adr, 1 mg/ml) and the secretion of GRS was determined at the indicated times. (C) RAW 264.7, HCT116 and HeLa cells were treated with Adriamycin (1 ug/ml) or TNF-a (1 ng/ml) with cycloheximide (CHX, 1 mg/ml), or incubated in glucose-deprived medium (−Glu) for the indicated times, and the secretion of GRS from the indicated cells was determined. (D) U937 cells were also tested for GRS secretion resulting from the indicated stimuli. (E) RAW 264.7 cells were treated with Adriamycin (Adr) and the secretion of three different ARSs (GRS, KRS and YRS) was determined.

Figure 9:
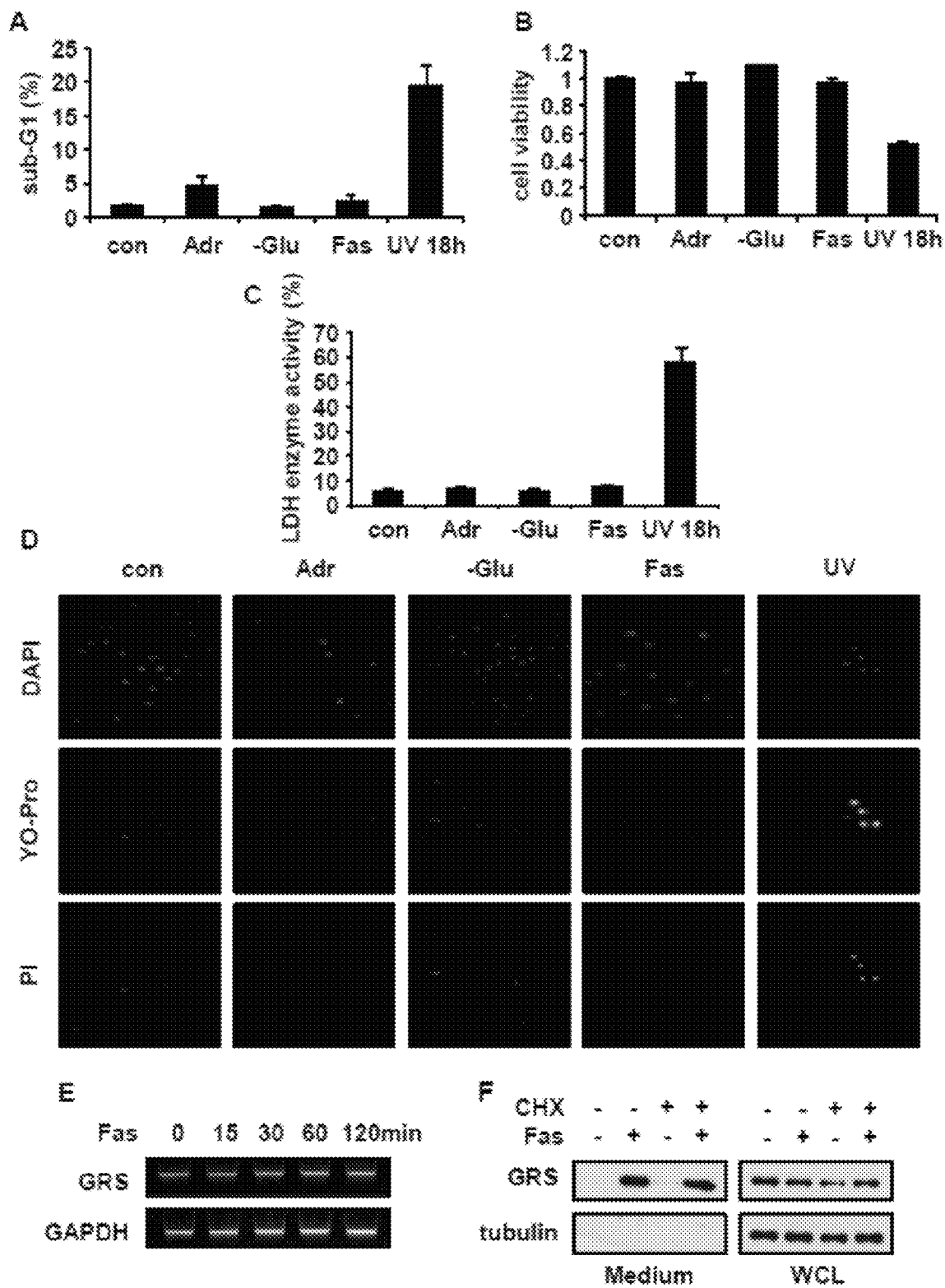
FIG. 9 shows that secretion of GRS does not result from cell lysis.

FIG. 9 shows that secretion of GRS does not result from cell lysis, related to FIG. 2. RAW264.7 cells were subjected to Adriamycin (Adr), glucose deprivation (−Glu) and Fas ligand (Fas) treatment for 4 h. As a positive control, the cells were irradiated by UV (200 J/m$^2$) and then incubated for 18 h. Cell death and viability were determined by sub-G1 cell population using FACS analysis (A), and MTT assay (B), respectively. (C) Extracellular LDH enzyme activity was determined with a LDH cytotoxicity kit (BioVision, Mountain view, Calif.) under the same conditions. (D) The plasma membrane integrity was determined by immunofluorescence staining Macrophages were fixed with 4% paraformaldehyde, treated with Yo-pro (green) and propidium iodide (red), and analyzed by immunofluorescence microscopy. Nuclei were stained with DAPI (blue). (E) U937 cells were treated with activating anti-Fas antibody (CH11 clone, 5 mg/ml) at the indicated times, and the levels of transcripts of GRS and GAPDH were determined by RT-PCR. (F) The cells were pre-treated with cycloheximide (CHX, 20 mg/ml) for 15 min and then activating anti-Fas antibody was added. After 4 h incubation, the proteins in the medium were precipitated with TCA and resolved by SDS-PAGE.

Figure 10:
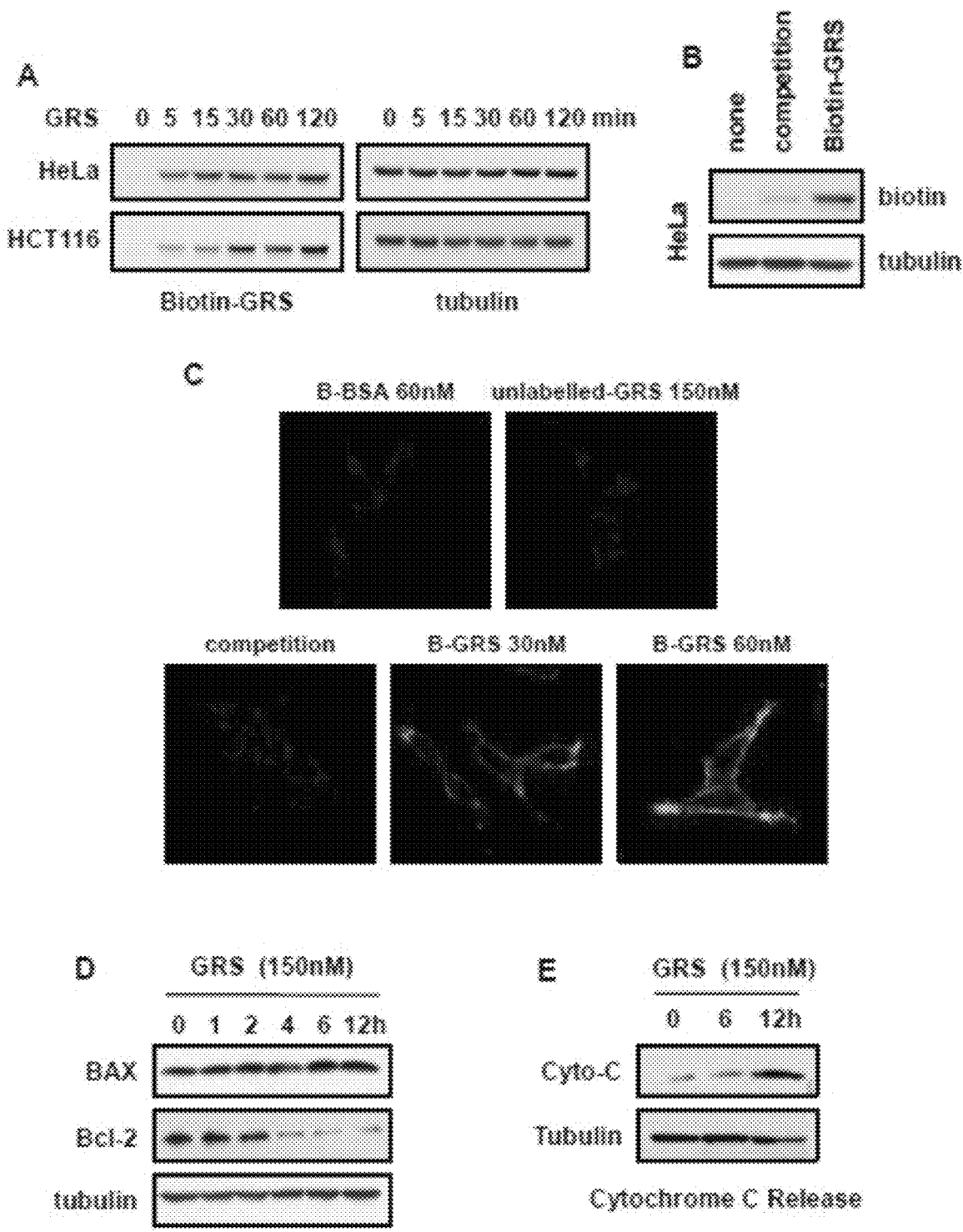
FIG. 10 shows identification of the targets cells by cell binding and effects of GRS on different mediators of apoptosis.

FIG. 10 shows identification of the targets cells by cell binding and effects of GRS on different mediators of apoptosis, related to FIG. 3. (A) HeLa and HCT116 cells were treated with biotinylated GRS (30 nM) at the indicated time and the cell binding of GRS was determined by immunoblotting. (B) To see whether the binding of biotinylated GRS is specifically competed by unlabelled GRS, HeLa cells were pre-treated with His-GRS (150 nM) or untreated for 15 min and then biotinylated GRS was added and incubated for 30 min. Cell binding of biotinylated GRS was monitored by immunoblotting. (C) HCT116 cells were incubated with the different concentrations of biotinylated GRS or BSA for 1 h. To see whether the binding of biotinylated GRS (30 nM) is specifically competed by unlabelled GRS, the cells were also pre-incubated with unlabelled GRS (150 nM). The binding of biotinylated GRS to HCT116 cells was monitored by immune-fluorescence staining with Alexa488-conjugated streptavidin. (D) The effect of GRS on BAX and Bcl-2 levels was determined by immunoblotting with their specific antibodies. (E) The effect of GRS on cytochrome C release from mitochondria was determined.

Figure 11:
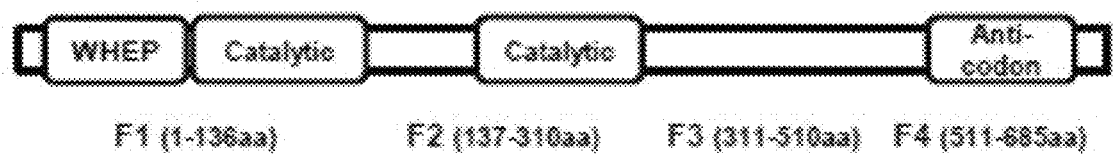
FIG. 11 shows determination of the cytokine-active domain in human GRS.
Figure 11:
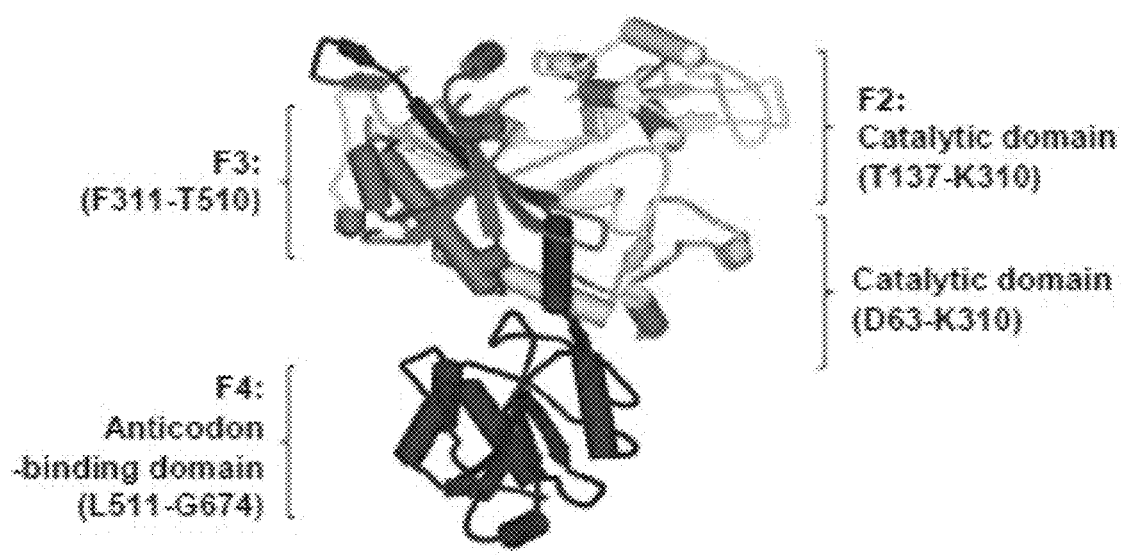
Figure 11:
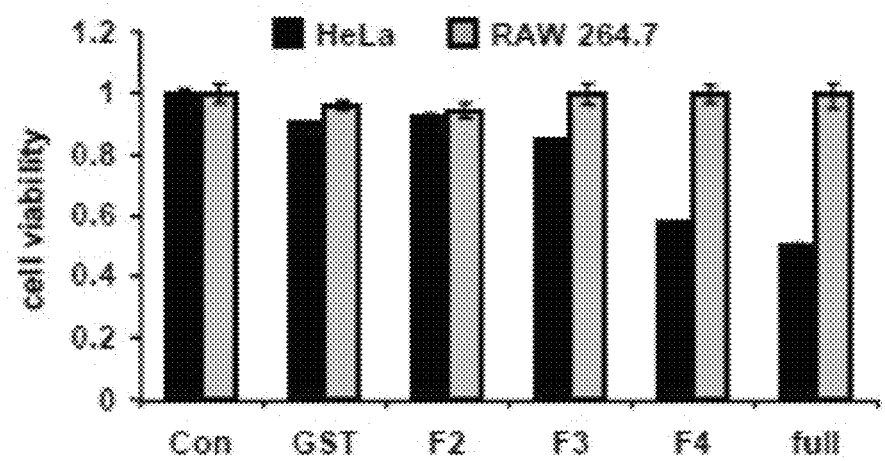

FIG. 11 shows determination of the cytokine-active domain in human GRS, related to FIG. 3. (A) the 685 aa human GRS consisting of the indicated functional domains was separated into four fragments (F1-4) that were purified as GST fusion proteins. The three fragments (F2-4) were obtained non-soluble forms except for F1. The WHEP domain is the multi-functional peptide domain attached to specific human aminoacyl-tRNA synthetases. The catalytic and anticodon-binding domains are located in F1/F2 and F4, respectively. (B) Three dimensional structure of human GRS (D63-G674) (Xie et al. 2006) and the deletion fragments of human GRS (F2-4) that were used for the cytokine assays are displayed in different colors using Accelrys DS Visualizer v2.0 (Accelrys Inc. USA). (C) The effect of GRS fragments on cell viability was compared using the MTT assay.

Figure 12:
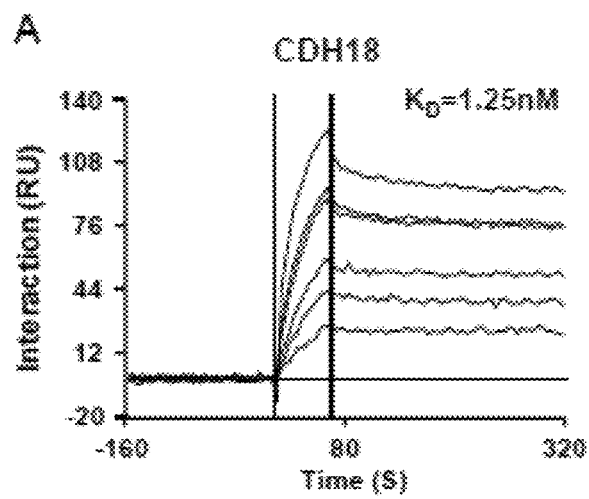
FIG. 12 shows determination of GRS binding to CDH6.
Figure 12:
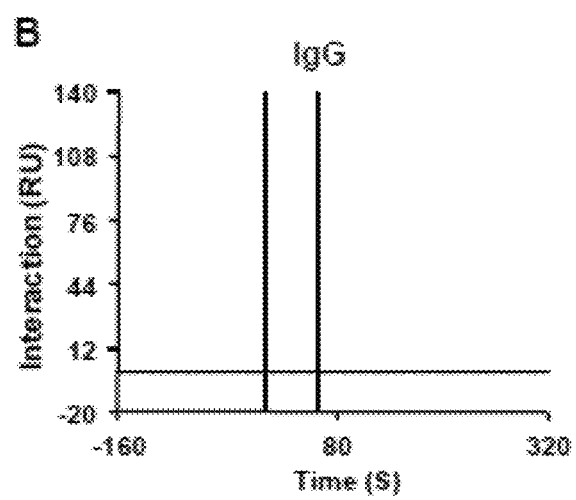
Figure 12:
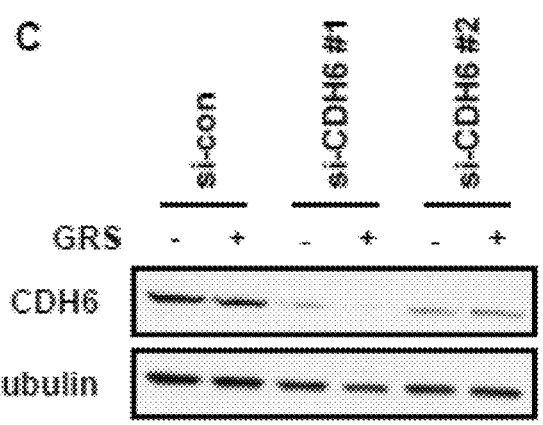

FIG. 12 shows determination of GRS binding to CDH6, related to FIG. 4. To calculate the dissociation constant ($K_D$), Fc-fusion cadherins (CDH18) (A) or Fc protein (IgG) (B) were immobilized to a gold chip and GRS (1 mM∼31.25 nM) was flowed on the surface. Binding between cadherin and GRS was determined by SPR as described in Methods. (C) HCT116 cells were transfected with non-specific siRNA (si-con) or siRNA targeting CDH6 (si-CDH6 #1 and #2) for FACS analysis, treated with GRS (30 nM), and the protein level of CDH6 was determined by immunoblotting.

Figure 13:
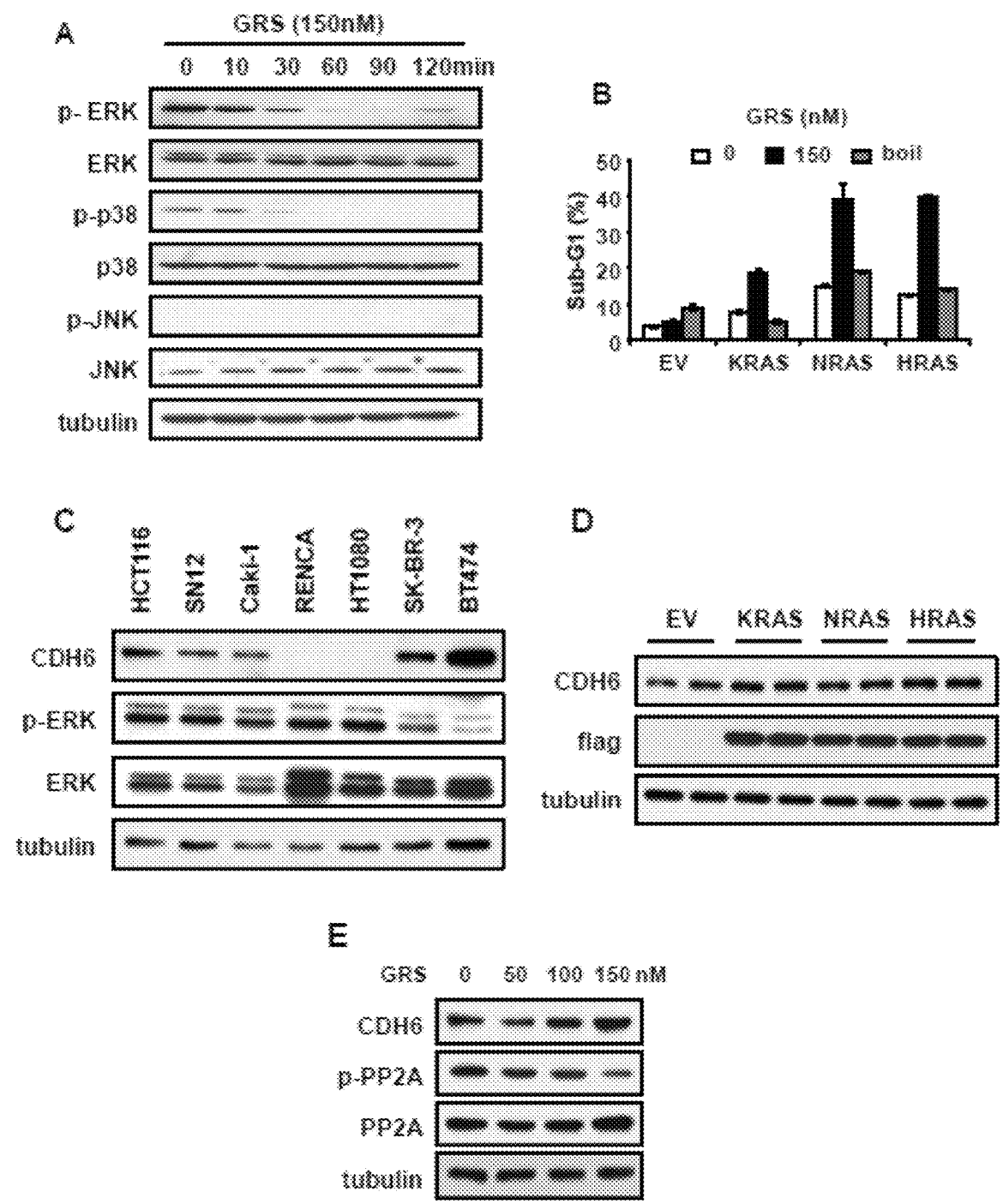
FIG. 13 shows correlation between CDH6 and phosphorylation of ERK.

FIG. 13 shows correlation between CDH6 and phosphorylation of ERK, related to FIG. 5. (A) HCT116 cells were treated with 150 nM GRS for the indicated times and the effect on the phosphorylation of ERK, p38 MAPK and JNK was determined by immunoblotting. (B) The effect of GRS on the death of Ras-transfected 293 cells was also determined at sub-G1 using flow cytometry. (C) Comparison of cellular levels of CDH6 and EKR phosphorylation in different cancer cell lines by immunoblotting. Tubulin is a loading control. (D) HEK293 cells were transfected with each of Flag-tagged K-, N- and H-RAS (oncogenic mutants) and their effect on CDH6 levels was determined by western blotting. (E) HCT 116 cells were treated with GRS and its effect on the phosphorylation of PP2A was determined by immunoblotting.

Figure 14:
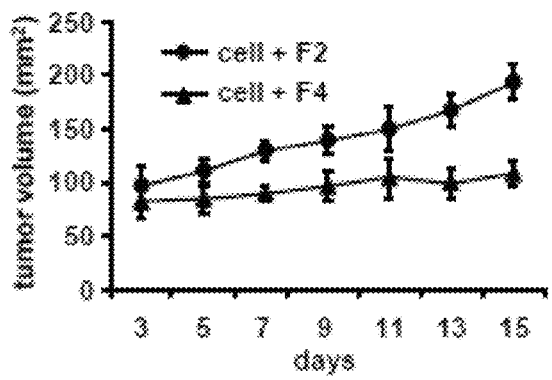
FIG. 14 shows determination of in vivo anti-tumor effects and toxicity of GRS and its domains.
Figure 14:
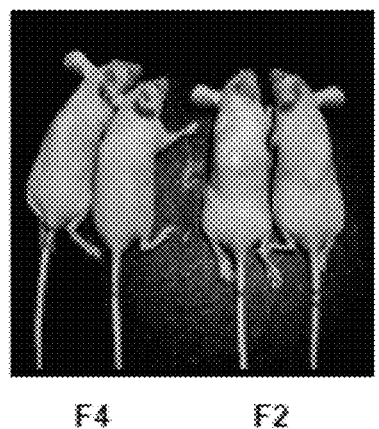
Figure 14:
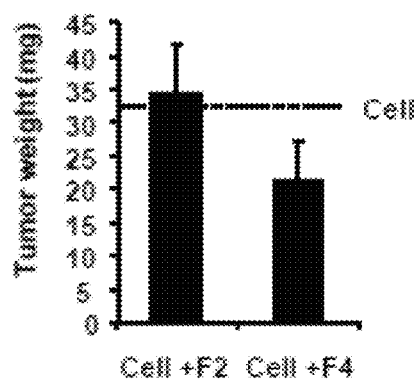
Figure 14:
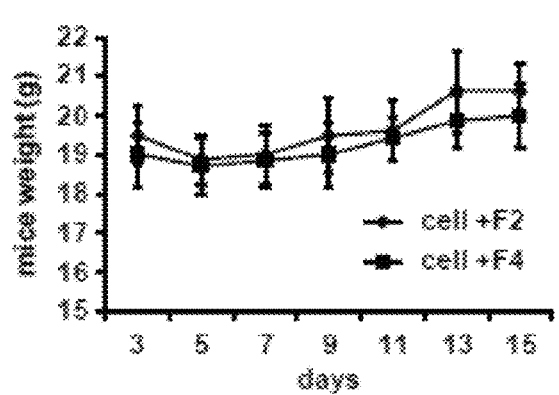
Figure 14:
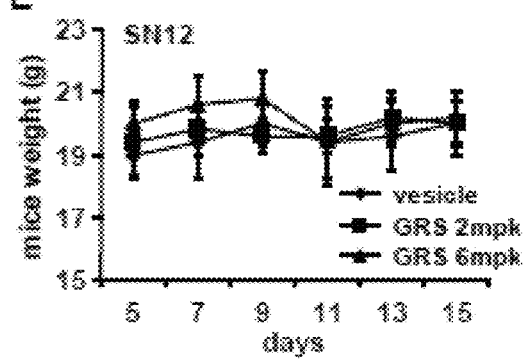
Figure 14:
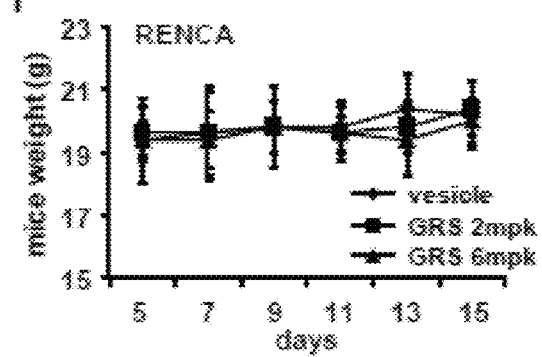

FIG. 14 shows determination of in vivo anti-tumor effects and toxicity of GRS and its domains, related to FIGS. 6 and 7. (A) HCT116 cells were injected into BALB/c nude mice as above with 20 mg of GRS F2 or F4 fragments (n=6 animal/group), and grown for 15 days. (B) Photograph of the two representative HCT116 xenograft tumor mice from the GRS F2 and F4 fragments 15 days after injection. (C) Tumor weights of the GRS F2 and GRS F4 fragments treated mice were determined 15 days after injection. (D) The body weights of the GRS F2 and GRS F4 fragments treated mice groups were measured at the indicated times (n=6). The body weights of SN12 (E) and RENCA cell (F) xenograft mice were measured (n=5). Error bars represent standard deviation.

<Experimental Procedures>

1. Secretion Assay

RAW 264.7 cells were cultivated in conditioned medium. The cells were collected and proteins were precipitated with 10% TCA. Precipitated proteins were separated by SDS-PAGE and transferred to PVDF membrane for immunoblot.

2. Co-Culture Assay

Co-culture experiments were performed by inoculating U937 or RAW264.7 cells (0.125×10$^6$ cells∼1×10$^6$/well) onto a layer of H460 or HCT116 cells (0.25×10$^6$/well) that had been cultured for 12 h in 6-well plates. The cells were then co-cultured for 6 h in serum-free medium. To assess the secretion of GRS, the cultured medium was harvested and then proteins were precipitated with 10% TCA. To demonstrate whether a physical interaction between macrophages/monocytes and tumors in co-culture was essential for GRS secretion, we used a 24-well Transwell cell culture chamber (Costar, #3470) fitted with inserts having 0.4 um pores. H460 cells were seeded in the chambers, and U937 cells were seeded in the inserts and incubated separately at a 1:2 H460:U937 ratio for 12 hours. The inserts were then transferred to the chambers in which the H460 cells were cultured. After 24 hours in culture, the inserts were removed and the medium was harvested for assay of secretion.

3. Apoptosis Assay

The tested cells were treated with different concentrations of recombinant GRS at the indicated times and harvested. After washing with PBS, the cells were fixed in 70% ethanol for 1 h and stained with 50 mg/ml propidium iodide solution in PBS. Twenty thousand cells per sample were read by fluorescence-activated cell sorting (FACS) using CellQuest software (BD Biosciences). For MTT assay, 20 ml of MTT solution (5 mg/ml) was added to 150 ml culture medium. After 4 h incubation, 200 ml DMSO was added. The absorbance at 570 nm was measured with a microplate reader (TECAN, Mannedorf, Swiss). The generation of active-caspase-3 from pro-caspase-3 was determined by immunoblotting using their respective antibodies (Cell Signaling, Beverly, Mass.).

4. Soluble Receptor Binding Assay

To identifying the receptor of GRS, a Maxisorp plate (Nunc, Rochester, N.Y.) was used for an ELISA detection. The plate were coated with purified his-tagged GRS (1 ug/ml) or BSA (1 ug/ml) in phosphate buffer saline and then blocked (PBS, 4% non-fat milk). Fc-fusion cadherin family proteins (1 ug/ml) were added to the plate and after washing with PBST (0.05% Tween20), the plates were incubated with anti-human IgG1 Fc-HRP (Thermo, Waltham, Mass.). The plates were then washed, added with TMB (3,3'5,5'-tetramethlybenzidine) solution and read at 450 nM using a microplate reader (TECAN, Mannedorf, Swiss).

And for confirming the interaction, purified Fc-CDH2, 6, 18 (1 ug/ml) were incubated with His-GRS (1 ug/ml) for 2 hours. The reactions were subjected to immunoprecipitation of the Fc-fused cadherins with protein A/G agarose, and analyzed by immunoblotting with anti-GRS to detect the complexes.

5. Xenograft Mouse Model

Animal experiments complied with the University Animal Care and Use Committee guidelines at Seoul National University. The tumorigenicity of HCT116, SN12 and RENCA was tested by subcutaneous injection of $3 \times 10^7$ cells in BALB/c nude female mice using a 20-gauge needle and allowed to grow. Tumor growth in animals was checked every 2 days, and if tumor formation was observed, tumors were measured using a caliper (Tumor volume was calculated as length×width$^2$×0.52). Renal tumor cells (SN12, RENCA) were grown for 5 days, and His-GRS protein was intra-peritoneal injected daily for 4 days. For the regression model, tumor cells were grown for 9 d, and His-GRS protein was then injected by intra-tumor injection. For the growth model, tumor cells were injected with or without His-GRS protein. After sacrifices, tumor weights were measured and embedded in optimal cutting temperature (OCT) compound for immunofluorescence staining. The frozen sections (10 um) were attached to the slides, treated with PBS and fixed with 4% paraformaldehyde, blocked with PBS containing 2% CAS, and stained with Yo-Pro-1 (Invitrogen) at 37° C. for 2 h. We washed the slides with PBS containing 0.1% Tween 20 (Sigma) and the nuclei were stained with DAPI (Invitrogen) at 37° C. for 20 min. The sections were mounted and observed via confocal immunofluorescence microscope (Nikon C-1 confocal microscope).

6. Cell Culture and Materials

RAW 264.7, SH-SY5Y, HSF (human skin fibroblasts), HEK293, BV2, MCF-7, SN12, SK-BR-3, BT474 and HeLa cells were grown in Dulbecco's modified Eagle's medium (DMEM) containing 10% fetal bovine serum and 50 mg/ml streptomycin and penicillin. For the cultivation of A549, H322, H460, HCT116, Caki-1, RENCA, HT1080 and Jurkat cells, we used RPM 1640 medium with the same supplements as above. Rabbit polyclonal antibody raised against the full-length human GRS (Abcam, Cambrage, UK) was used for Western blot analysis. Si-RNAs of 5'-UUUCAUA-GAACUCA GCAAAUUCUGG-3' and 5'-UAAUAAUGAA-GAGAUCUCCUGCUCC-3' targeting CDH6 was obtained from Invitrogen (Carlsbad, Calif.). Stealth universal RNAi (Invitrogen) was used as a negative control.

7. Preparation of Recombinant Human GRS

Human GRS cDNA encoding 685 amino acids was subcloned into pET-28a (Novagen, Madison, Wis.) at sites for EcoRI and XhoI restriction enzymes, and overexpressed in *E. coli* Rosetta (Novagen) by IPTG induction. His-tagged GRS was then purified using nickel affinity chromatography (Invitrogen) following the manufacturer's instruction. GST-GRS fragments were also expressed in *Escherichia coli* Rosetta by IPTG induction. GST-fusion proteins were purified using glutathione-sepharose in the PBS buffer containing 0.5% Triton X-100. To remove lipopolysaccharide (LPS), the protein solution was dialyzed in 10 mM pyrogen-free potassium phosphate buffer (pH 6.0) containing 100 mM NaCl. After dialysis, the GRS-containing solution was loaded to polymyxin resin (Bio-Rad) pre-equilibrated with the same buffer, incubated for 2 hours, and then eluted. To further remove residual LPS, the solution was dialyzed again in PBS containing 20% glycerol, and filtered through an Acrodisc unit with the Mustang E membrane (Pall Gelman Laboratory, Ann Arbor, USA)

8. GRS Secretion Assay

RAW 264.7 cells were cultivated to 70% confluency. The cells were then washed twice and further cultivated in serum-free or glucose-deprived DMEM medium. In addition, we added Adriamycin (1 mg/ml, Calbiochem, San Diego, Calif.), TNF-a (1 ng/ml, BD Pharmingen, San Diego, Calif.) with cycloheximide (1 ug/ml, Sigma St. Louis, Mo.), Fas-ligand (10 ng/ml, Millipore) or Anti-Fas antibody (5 ug/ml, clone CH11, Millipore, Billerica, Mass.) to the serum-free medium. The culture media was collected at the indicated times, and centrifuged at 500 g for 10 minutes and 20,000 g for another 15 minutes to remove contaminants. Proteins were precipitated from the supernatants with 10% TCA for 12 hours at 4° C. and then centrifuged at 18,000 g for 15 minutes. The pellets were harvested, re-suspended with 100 mM HEPES buffer (pH 8.0), separated by 10% SDS/PAGE and the proteins were transferred to PVDF membrane for immunoblotting with polyclonal anti-GRS antibodies. Some of the supernatants were pre-cleared with an anti-IgG antibody, and incubated with anti-GRS antibodies for 2 hours at 4° C. Protein A agarose (Invitrogen) was then added, and the mixture was incubated for 4 hours at 4° C. The protein A agarose beads were next precipitated and washed 3× with 50 mM Tris-HCl buffer (pH 7.5) containing 150 mM NaCl, 1% Triton X-100, 10 mM NaF, 1 mM sodium orthovanadate, 10% glycerol and protease inhibitors (Calbiochem) and the bound proteins were eluted using the sample buffer.

9. Cell Necrosis Assay and Assessment of Plasma Membrane Integrity

RAW264.7 cells were seeding onto a 6-well dish and incubated for 12 hours. Cells were then washed twice and further incubated with indicated conditioned medium. To measure the LDH content of the culture media, the conditioned medium was collected and then centrifuged at 2,000 g for 15 min. The supernatant was harvested and the LDH enzyme activity was measured using a LDH-cytotoxicity assay kit (BioVision, Mountain view, Calif.), following the manufacturer's instructions. By expressing the released LDH as a percentage of the total cellular LDH, cell viability could be calculated. To monitoring the membrane integrity by immunofluorescence staining, cells were seeded on 22×22 mm cover glasses and incubated for 24 hours. The culture dishes were washed twice by PBS and incubated with the indicated conditioned medium. The cells were fixed for 10 min in 4% paraformaldehyde, and rinsed 2× with cold PBS. The cover glasses were incubated with 3% CAS in PBS for 30 minutes and then incubated with a 50 mg/ml propidium iodide, 5 uM Yo-Pro-1 (Invitrogen) solution in PBS for 1 h. Nuclei were stained using 4',6-diamidino-2-phenylindole dihydrochloride (DAPI). The cells were mounted and observed via fluorescence microscopy (Nikon C-1 confocal microscope).

10. Cell Binding Assay

Cells were seeded onto 6-well dishes and incubated for 12 hours. Biotinylated GRS was then added to the culture medium and further incubated for the indicated times. The cells were washed 4× with cold PBS and then lysed in 50 mM Tris-HCl (pH 7.4) lysis buffer containing 150 mM NaCl, 2 mM EDTA, 1% Triton X-100, 1% sodium deoxycholate, 10 mM NaF, 1 mM sodium orthovanadate, 10% glycerol and protease inhibitors, and the mixture was centrifuged at 18,000 g for 15 minutes. The extracted proteins (30 mg) were resolved by SDS/PAGE, and detected by streptavidin-coupled Horseradish peroxidase (HRP) (Pierce, Rockford, Ill.). For biotinylation, recombinant GRS (1.5 mg) was incubated with 0.25 mg sulfo-NHS-SS-biotin (Pierce) in PBS for 2.5 hours at 4° C. To monitor cell binding of GRS by immunofluorescence staining, cells were seeded on 22×22 mm cover glasses and incubated for 12 hours. The culture dishes were then incubated with biotinylated GRS and biotinylated BSA for 1 h. The cells were fixed for 10 minutes in 4% paraformaldehyde, and rinsed 2× with cold PBS. The cover glasses were incubated with 3% CAS in PBS for 30 minutes and the bound biotin-labeled GRS was then captured with Alexa488-conjugated streptavidin (Invitrogen). The cells were mounted and observed via confocal immunofluorescence microscope. To monitoring cell binding of GRS by flow cytometry, cells were transfected with specific si-RNA and incubated for 48 hours. Cells which were treated as described above were washed 3× with PBS, and stained with Alexa488-conjugated streptavidin (Invitrogen) in FACS buffer (PBS containing 2% BSA) for 1 hour. After then, cells were washed 3 times with PBS. Cells were analyzed by flow cytometry using CellQuest software (BD Biosciences, Mountain view, Calif.).

11. Surface Plasmon Resonance Analysis

Binding of GRS to the cadherin-Fc fusion proteins was determined by the SPR technique using a ProteOn XPR36 Protein Interaction Array System (BioRad). CDH6, 18 and IgG (negative control) were immobilized on a GLC gold chip via the amine coupling method according to the manufacturer's instructions (~1000 RU each). Various concentrations of purified GRS were applied to the flow cell in phosphate-based saline containing 0.005% Tween 20 at 100 mL/min for 60 seconds and then dissociated for 600 seconds. The binding was determined by the change in resonance units (RU), where one resonance unit is defined as 1 pg/mm$^2$. The Sensogram was processed by subtracting the binding response recorded from the control surface. The equilibrium dissociation constants were calculated using Proteon Manager software (ver. 2.1). The data was evaluated using a Langmuir 1:1 binding model.

12. RT-PCR Assay

Cells were incubated on six-well dishes for 12 h, washed twice, and then stimulated. Total RNAs were extracted by using RNeasy mini kit (QIAGEN, Valencia, Calif.) with random hexamer, and RT-PCR was performed with the primers specific to GRS and GAPDH.

13. Cytochrome C Release Assay

Translocation of cytochrome C was examined using western blotanalysis. HeLa cells were incubated with 150 nM GRS for indicated times and the harvested cells were resuspended in 20 mM of HEPES (pH 7.5) hypotonic buffer containing 10 mM potassium chloride, 1.5 mM MgCl$_2$, 0.5 mM EDTA, 1 mM DTT and protease inhibitors (Calbiochem) for 5 min on ice, and then homogenized 6 times. The samples were centrifuged at 10,000 g for 10 min. The proteins in the supernatants were subjected to SDS-PAGE and were then probed with polyclonal antibodies against cytochrome C and tubulin.

<Results>

1. Secretion of GRS from Macrophages

GRS was detected in the serum of 3 different human subjects and of 2 different CL57BL/6 mice (FIG. S1A). Consistent with a lack of cell lysis, neither of b-tubulin, LDH or GAPDH was detected in the same sample. These observations motivated us to learn more about the physiological function of secreted GRS. To have clues to the physiological function of secreted GRS in cancer microenvironment, we examined whether secretion of GRS could be detected from cultured cells and, if so, whether such secretion was specific to a cell type. Six different cell lines (H322, A549, HEK293, HCT116, RAW 264.7, and HeLa) were incubated in a serum-free medium for 12 h, and the secreted proteins were precipitated from the medium using TCA. The precipitated proteins were determined by western blot analysis with anti-GRS polyclonal antibodies (a-GRS). Among the 6 tested cell lines, GRS was detected only in the culture medium of murine macrophage cell line RAW 264.7 (FIG. 1A). Under the same conditions, we observed no release of tubulin into the medium, suggesting that the presence of GRS in the medium was not due to cell lysis (FIG. 1A).

To further confirm secretion of GRS, proteins in the serum-free medium of cultured RAW 264.7 cells were immunoprecipitated and blotted with a-GRS. Full-length GRS was specifically detected in the immunoprecipates obtained with a-GRS, but not with mock IgG (FIG. 1B). Analysis of the time-course of secretion showed that, for RAW 264.7 cells, GRS was detected in the medium after 12 h starvation and was increased somewhat more at later times (FIG. 1C).

Given the apparent specificity of GRS secretion, we investigated other immune cells, such as T lymphocyte Jurkat cells, microglia-derived BV2 cells, and macrophage-like U937 monocytes. GRS was detected only in the conditioned medium of U937 as well as RAW 264.7 cells, but not of Jurkat or BV2 cells (FIG. 1D). Thus, GRS was secreted from macrophages/monocytes under starvation conditions.

2. Different Apoptotic Stresses Induce Secretion of GRS

To investigate whether GRS secretion can be induced by stimuli other than starvation, we treated RAW 264.7 cells with signaling molecules. These included estrogen, which regulates cytokine production in macrophages (Carruba et al., 2003) TNF-a, which influences macrophage differentiation (Witsell and Schook, 1992) and EGF, which can be secreted from macrophages and tumor cells. In addition, we tested Adriamycin to induce cell death through DNA damage. After 6 h of treatment with each of these four 'ligands', only Adriamycin induced secretion of GRS (FIG. S1B). This result suggested that apoptotic stress was important for GRS secretion. With this possibility in mind, we treated RAW 264.7 cells with other apoptotic stresses and compared the time course of GRS secretion. In addition to Adriamycin, both glucose-deprivation and treatment with TNF-a with cycloheximide resulted in time-dependent secretion of GRS from RAW 264.7, but not from human colon cancer HCT 116 or cervical cancer HeLa cells (FIG. S1C). These three apoptotic stresses also induced GRS secretion from U937 cells (FIG. S1D). In contrast to GRS, no secretion of KRS or YRS, other known AARS cytokines, was detected in Adriamycin-treated U937 cells (FIG. S1E).

Because GRS secretion was observed immediately after the onset of any of three different apoptotic stresses, it is unlikely that secretion of GRS resulted from cell lysis. To confirm this conclusion, we determined cell lysis by monitoring the sub-G1 cell cycle population and by performing an MTT (3-(4,5-dimethylthiazol-2-Yl)-2,5-diphenyltetrazolium bromide) assay. We found that none of the apoptotic stresses seriously affected cell cycle and viability (FIGS. S2A and B). We also measured the activity of cytosolic lactate dehydrogenase (LDH) in the conditioned medium. The LDH activity in the medium was less than 10% of that in the cell extracts and did not increase in the conditioned medium (FIG. S2C). Because cell membrane integrity is disrupted in apoptosis or necrosis, we stained RAW 264.7 cells with membrane-permeable Yo-Pro and also stained with membrane-impermeable propidium iodide (Bhatnagar et al., 2007). Neither dye stained the nuclear structure after induction of apoptotic stresses. However, both dyes stained nuclear DNA when macrophages were irradiated with UV (200 J/m$^2$) and then incubated for 18 h (FIG. S2D). These results are consistent with GRS secretion not arising from cell lysis or membrane rupture.

3. GRS Secretion can be Induced by Fas Ligand Derived from Cancer Cells

Among other functions, macrophages play a critical role in immune surveillance of the cancer cell microenvironment. To explore whether the secretion of GRS from macrophages was affected by proximity to tumor cells, we set up a co-culture system with H460 human large cell lung tumor and U937 cells. Significantly, secretion of GRS, but not KRS, YRS and WRS, was observed and the amount of secretion increased as the number of added U937 cells was increased (FIG. 2A).

GRS secretion was also detected in the co-culture systems with HCT116 and U937 cells, and with H460 and RAW 264.7 cells (FIGS. 2B and C). In addition, we used bone marrow-derived macrophages (BMDM) for the co-culture system. In this ex-vivo assay, GRS secretion was also seen (FIG. 2D). Next, to determine whether GRS secretion required physical contact between tumor and macrophage cells, we used conditioned medium and Transwell culture dishes as described previously (Khodarev et al., 2002). Significantly, conditioned medium harvested from H460 cells induced GRS secretion from RAW 264.7 and U937 cells (FIG. 2E). We also separated U937 and H460 cells by incubating U937 cells in the inserts and H460 cells in the chambers of Transwell dishes. Secretion of GRS increased according to the number of U937 cells (FIG. 2F). These results suggest that secretion of GRS does not require physical contact between cancer and macrophage cells.

Because tumor cells can escape immune surveillance by secreting Fas ligand (Igney and Krammer, 2002), and given that secretion of GRS was induced by apoptotic stresses and by co-cultivated tumor cells, we examined whether Fas ligand was involved in GRS secretion. To test this possibility, we added agonistic Fas antibody to U937 cells in conditioned medium, and determined whether this addition triggered secretion of GRS. Indeed, after the treatment, GRS accumulated in the medium in a time-dependent way (FIG. 2G). To confirm the correlation between Fas ligand and GRS secretion, we also added an antagonistic Fas antibody to the co-culture system. After the neutralizing effect, GRS secretion was decreased in the medium (FIG. 2H). However, there was no evidence that Fas affected the transcription of the gene for GRS, as determined by an RT-PCR analysis (FIG. S2E). Finally, blockage of de novo protein synthesis with cycloheximide did not inhibit the secretion of GRS (FIG. S2F). These results are consistent with a model of GRS being secreted by Fas ligand derived from cancer cells.

4. Cell Binding of Secreted GRS

To determine the target cells of the secreted GRS, we incubated human breast cancer MCF7, HeLa, HCT116, and RAW 264.7 cells with different concentrations of biotinylated GRS. With this assay, biotinylated GRS was detected as bound to HCT116, HeLa, and RAW 264.7 cells in a dose-dependent manner, but was not to MCF7 cells (FIG. 3A). (Under the same conditions, biotinylated BSA was not detected as bound to any of the 4 cell types.) Next, we determined the time course of GRS binding to HeLa and HCT116 cells. Binding of biotinylated GRS was detected after 5 min of incubation with these cells and increased to a maximum at 15-30 min (FIG. S3A). To confirm the specificity of cell binding by GRS, the cells were pre-incubated with unlabeled GRS for 15 min, after which biotinylated GRS was added. The biotin signal was significantly suppressed when the cells were pretreated with unlabeled GRS (FIG. S3B). Cell binding of GRS was further monitored by immune-fluorescence staining. The staining intensity increased according to the amount of GRS, but was reduced by the addition of unlabeled GRS (FIG. S3C). Thus, the staining intensity was specifically attributable to GRS binding. Collectively our results show that specific tumor cells and macrophages are targets of secreted GRS.

5. Pro-Apoptotic Effect of GRS on Tumor Cells.

Given that GRS secretion is induced by apoptotic ligands such as Fas, which are secreted from tumor cells, and that secreted GRS binds to tumor cells, we investigated whether GRS exerted a paracrine effect. We monitored cell viability and death by using an MTT assay and, separately, by monitoring the sub-G1 cell population with flow cytometry. When treated with GRS, the viability of HCT116, but not of RAW 264.7 cells, decreased in a dose-dependent manner (FIG. 3B). The sub-G1 population of HCT116, but not of RAW 264.7 cells, was also increased by treatment with GRS (FIG. 3C). Apoptotic cell death resulting from GRS treatment was confirmed by the activation of caspase-3 (FIG. 3D). We also tested the apoptotic activity of GRS by monitoring cellular levels of Bax and Bcl-2, and on the release of cytochrome c. Although GRS did not affect the cellular level of Bax, it reduced the level of the anti-apoptotic mediator Bcl-2 (FIG. S3D) and enhanced the release of cytochrome c that are the known signatures of cell death (FIG. S3E). Because heat-inactivated GRS did not exert any pro-apoptotic effects in these assays (FIGS. 3C and D), the native conformation of GRS appears to be important for its pro-apoptotic activity.

To investigate whether GRS can induce cell death in a physiological environment, we co-cultured HCT116 and U937 cells by using Transwell chambers with or without anti-GRS antibody. The viability of HCT116 cells decreased on co-cultivation with U937 cells. However, the addition of a-GRS compromised the effect of GRS on the viability of U937 cells (FIG. 3E). In further experiments, GRS reduced the viability of different tumor cell lines, including human alveolar adenocarcinoma A549, H460, HCT116, and HeLa cells. However, GRS had no effect on the viability of MCF-7, neuroblastoma SH-SY5Y cells, or on human skin fibroblasts (HSF), human embryonic kidney HEK293, or RAW 264.7 cells (FIG. 3F). Thus, GRS exerts its pro-apoptotic activity on a specific set of cancer cells.

6. Anticodon-Binding Domain is Responsible for Apoptotic Effect

To identify the domain responsible for the pro-apoptotic activity of GRS, we used the known x-ray crystal structure of human GRS to guide construction of 4 different fragments (FIGS. S4A and B). Among the 4 different fragments, we obtained 3 (F24) soluble forms. (Owing to low stability and solubility, we failed to obtain the N-terminal fragment of GRS (F1).) Fragments F24 were separately added to HeLa and RAW 264.7 cells. At a concentration of 150 nM both GRS and the 175 amino acid C-terminal anticodon-binding domain (ABD) decreased the viability of HeLa cells. In contrast, neither fragment F2 nor F3 was comparable in activity to GRS or ABD. This result suggested that the ABD harbors the pro-apoptotic cytokine activity of GRS (FIG. S4C).

7. Cadherin-6 as a Functional Receptor for GRS

Given that the secreted N-terminal-truncated WRS binds to VE-cadherin to inhibit angiogenesis (Tzima et al., 2005), and that several cadherins (CDHs) are known to be associated with tumor cell survival and malignancy (Cavallaro and Chrostofori, 2004), we tested whether GRS can bind to any of 11 different CDH proteins. The interaction of His-GRS with the extracellular domains of 11 different cadherins individually fused to the Fc fragment of human IgG1 was determined by ELISA assays. This screening identified specific binding of GRS to CDH6 and CDH18, but not to the remaining CDHs (FIG. 4A). GRS binding to CDH6 and CDH18, but not to CDH2, was confirmed by an in vitro pull-down assay (FIG. 4B).

The binding affinity of GRS to CDH6 and 18 was measured by surface plasmon resonance assay. GRS bound to CDH6 and CDH18 with a KD=3.4 and 1.25 nM, respectively (FIG. 4C and FIG. S5A), but not to IgG protein (FIG. S5B). In further studies, only the ABD domain encoded by fragment F4, and not fragments F2 or 3, bound to CDH6 in a pull-down assay (FIG. 4D). And we also confirmed that only F4 fragment bound to CDH6, not F2 or F3 fragment using ELISA assay (F1 fragment is insoluble) (FIG. 4I).

Because CDH6 appears to be implicated in the etiology of hepatocellular carcinoma, renal carcinoma, and small cell lung cancer (SCLC) (Shimoyama et al., 1995; Li et al., 2005), we investigated whether CDH6 can act as a functional receptor for GRS in tumor cells. First we determined the protein expression level of CDH6 in the tested tumor cell lines. We found that CDH6 expression was up-regulated in the GRS-sensitive cancer cell lines (HCT116, H460, and HeLa), but not in GRS-insensitive cancer cell lines (MCF7 and SH-SY5Y) (FIG. 4E). Using western blot analysis (FIG. 4F) and flow cytometry, we found that GRS binding to HCT116 cells was reduced when the CDH6 transcript was suppressed by its specific si-RNA, but not by a non-specific control siRNA (FIGS. 4G and S5C). We then tested whether the soluble extracellular domain of CDH6 could offset the apoptotic activity of GRS. We found that the effect of GRS on the viability of HCT116 cells was diminished by the addition of soluble CDH6 receptor protein (FIG. 4H). Our results suggest CDH6 is a functional receptor for GRS in tumor cells.

8. GRS Induces Cell Death Via Suppression of ERK Activation

To investigate the mechanism by which GRS treatment induces cell death, we treated HCT116 cells with GRS and determined the effect on 3 mitogen-activated protein kinases ERK, p38 MAPK, and JNK. We found that the levels of phosphorylated ERK and p38 MAPK, but not JNK, were decreased by GRS treatment in a dose- and time-dependent manner (FIGS. 5A and S6A). Since activation of ERK is known to be involved in cancer cell proliferation and survival (Warner and McIntosh, 2009), we tested whether the apoptotic susceptibility of cancer cells to GRS is determined by the activation status of ERK. Interestingly, GRS-sensitive HCT116, H460, and HeLa cancer cells showed enhanced phosphorylation of ERK, whereas GRS-insensitive SH-SY5Y and MCF7 cancer cells did not (FIG. 5B). This result provided a positive correlation between the activation status of ERK and the sensitivity of the cancer cell to GRS.

Among the 3 GRS-sensitive cell lines, HCT116 and H460 cells are known to contain KRAS mutations that lead to activation of ERK. The Ras-Raf-MEK-ERK cascade is a key signaling pathway for cancer cell proliferation and survival (Roberts and Der, 2007). We therefore tested whether activation of ERK by oncogenic Ras mutants renders apoptotic sensitivity to GRS treatment. For this purpose, we chose HEK293 cells that are normally insensitive to treatment with GRS. Three different Ras-active mutants (KRAS, HRAS, and NRAS) were introduced into HEK293 cells and stable cell lines were established. The selected stable cell lines expressed each of the transfected Ras mutants and, after introduction of the mutations, showed sharply increased phosphorylation of ERK. We then treated the cell lines with GRS and studied the effect on phosphorylation of ERK. Strikingly, in all 3 cell lines, GRS suppressed phosphorylation of ERK (FIG. 5C). Next, we examined whether cell viability and death of the Ras transfected HEK293 cells were affected by GRS treatment. Using the MTT assay and, separately, flow cytometry, we found that treatment with GRS suppressed cell viability and increased the death of the three Ras transfectants. In contrast, treatment with GRS had no effect on the control HEK293 cells (FIGS. 5D and S6B). Our results are consistent with the hypothesis that, by the dephosphorylation of activated ERK, GRS can induce apoptosis of Ras-activated tumor cells.

We then examined whether the negative regulation of ERK phosphorylation by CDH6 is universally applied to all cell types. Among the tested cell lines, HCT116, renal carcinoma SN12, breast carcinoma cell SK-BR-3 and renal carcinoma Caki-1 showed high levels of both CDH6 and phosphorylated ERK (FIG. S6C). However, renal cancer cell line RENCA, fibrosarcoma cell line HT1080, showed high ERK phosphorylation levels with undetectable levels of CDH6 levels. In contrast, despite the high levels of CDH6, breast carcinoma cell line BT474, showed low levels of ERK phosphorylation. In addition, transfection of HEK293 cells with K-, N- and HRAS did not affect the cellular levels of CDH6 (FIG. S6D). All of these results imply that the cellular level of CDH6 is not directly linked to the activation of ERK.

We tested the susceptibility of the various cell lines to the apoptotic stress of administered GRS. Only cells with high levels of both CDH6 and ERK phosphorylation were susceptible to GRS-induced apoptosis (FIG. 5D). The correlation of GRS-induced apoptosis with high levels of both CDH6 protein and ERK phosphorylation extended to 8 cell lines.

Phosphorylation of ERK is regulated not only by the upstream MEK1 and 2 kinase, but also by phosphatases (Keyse, 2000; Gronda et al., 2001; Wang et al., 2003). However, the phosphorylation of MEK was not reduced by GRS treatment (data not shown). To see whether GRS can suppress ERK phosphorylation by activating a phosphatase, we treated HCT116 cells with four different phosphatase inhibitors and checked how they would affect the GRS-induced phosphorylation of ERK. Among the four phosphatases, the okadaic acid phosphatase 2A (PP2A) inhibitor specifically blocked GRS-dependent inhibition of ERK (FIG. 5E). GRS treatment also weakened the interaction between CDH6 and PP2A (FIGS. 5F and G) and reduced the phosphorylation of PP2A (FIG. S6E) to thereby enhance the activity of PP2A (Chen et al., 1992 Janssens and Goris, 2001). Concomitantly, the interaction between PP2A and ERK was increased (FIG. 5H). These results suggest that GRS can release PP2A from CDH6 and then induce PP2A activity, which then dephosphorylates ERK.

9. Anti-Tumor Effects of GRS In Vivo

To investigate the possibility that GRS may also be active in vivo, we tested GRS in a xenograft model using HCT116 cells. In the first experiments, HCT116 cells were injected into Balb/C nude mice, and tumors were grown until they reached an average size of 100 mm2. On day 9, either vehicle alone or 10 mg or 20 mg GRS was directly delivered to the tumors. Tumor volumes increased approximately 2.5-fold in the vehicle-treated group by day 21. In contrast, GRS-injection reduced tumor volumes in a dose-dependent manner (FIGS. 6A and B). Tumor weights were decreased to 56% and 34%, after treatment with 10 μg and 20 μg of GRS, respectively (FIG. 6C). In addition, the lack of change in animal weight and posture suggested that no overt toxicity occurred because of the administration of GRS (FIGS. 6B and D). Immunofluorescence analysis was used to investigate whether apoptosis was induced in tumors injected with 20 mg GRS. A higher number of Yo-Pro-1-positive tumor cells appeared in the GRS-treated tumor tissues than in the control tissues (FIG. 6E).

Next, we examined the effect of GRS on the initial stage of tumorigenesis. HCT116 cells were injected into nude mice, with or without GRS (20 μg). While tumor volumes increased up to 185 mm$^2$ in the vehicle control, tumors failed to grow when GRS was co-injected with the cells (FIGS. 6F and G). Compared with the control vehicle, tumor weight was decreased by 46% after treatment with GRS (FIG. 6H). Apoptosis in HCT116 cells of the GRS-treated animals was clearly seen (FIG. 6J). Again, as evidenced by a lack of change in animal weight and posture, no overt toxicity due to the administration of GRS, was observed (FIGS. 6G and I).

The ABD (F4) but not catalytic domain (F2) of GRS was sufficient to elicit the apoptotic activity in a cell-based assay. To test whether this distinction between two domains of GRS was seen also in vivo, HCT116 cells were injected into Balb/C nude mice together with 20 mg of catalytic domain or of ABD fragment. Fragment F4, but not F2, inhibited tumor growth (FIGS. S7A and B). The reduction of tumor weight was comparable to that achieved with injection of GRS alone 37% versus 46% (FIG. S7C). Both fragments gave little toxicity resulting from their injection (FIG. S7D). Thus, the apoptotic activity of ABD seen with in vitro cell-based assays was recapitulated in vivo.

10. CDH6-Dependent Anti-Tumor Effects of GRS In Vivo

The robust apoptosis activity induced by GRS on tumorigenic cells eliciting the CDH6 and ERK phosphorylation markers raised the possibility that anti-tumor activity of GRS in vivo may be CDH6 dependent. To test this possibility, we examined cell binding of GRS in renal cancer cells, which were associated with CDH6. GRS bound only to renal cancer cells, SN12, expressing high level of CDH6, but not to RENCA cells that expressing low level of CDH6 (FIGS. 7A and C), suggesting that the activity of GRS would depend on the expression levels of CDH6. This notion was further confirmed by in vivo anti-tumor activity test of GRS using xenograft model with these two cells lines. For this, we transplanted SN12 and RENCA cells into nude mice and injected GRS protein at two different doses (2 mg/kg and 6 mg/kg) 4 times by intraperitoneal injection. In these two models, GRS inhibited only the growth of SN12 (FIG. 7B), but not of RENCA cells (FIG. 7D). Tumor weights of SN12 were decreased to 36% and 58%, after treatment with 2 mg/kg and 6 mg/kg of GRS, respectively. However, tumor weights of RENCA were decreased only to 7% and 15% at the same conditions (FIG. 7E). The lack of change in animal weight suggested that no overt toxicity occurred in both xenograft mouse models (FIGS. S7E and F). To determine the effect of GRS on the status of ERK treatment, we also monitored the phosphorylation of ERK by western blotting. In SN12 xenograft samples, dephosphorylation of ERK was clearly observed in GRS treatment group (FIG. 7F), further validating that the CDH6-dependent apoptotic activity of GRS seen with in vitro cell-based assays was recapitulated in vivo.

What is claimed is:

1. A method of screening for an agent treating cancer comprising:
   measuring a first binding affinity between GRS (glycyl-tRNA synthetase) or a GRS fragment, and CDH (cadherin);
   measuring second binding affinities between the GRS or the fragment, and CDH, in the presence of test agents;
   comparing the first binding affinity to each of the second binding affinities; and
   identifying the test agents that change the binding affinity between the GRS or fragment, and the CDH, by using the result of the comparison,
   wherein the CDH is CDH6 or CDH18.

2. The method of claim 1, wherein the cancer is selected from the group consisting of malignant melanoma, leukemia, colon cancer, lung cancer, liver cancer, stomach cancer, esophagus cancer, pancreatic cancer, gall bladder cancer, kidney cancer, bladder cancer, prostate cancer, testis cancer, cervical cancer, endometrial carcinoma, choriocarcinoma, ovarian cancer, breast cancer, thyroid cancer, brain tumor, head or neck cancer, skin cancer, lymphoma, and aplastic anemia.

3. The method of claim 1, wherein the GRS is an amino acid sequence selected from the group consisting of SEQ ID NO. 1, 5, 6, 7, 8, 9, and 10.

4. The method of claim 1, wherein the fragment is an amino acid sequence represented by SEQ ID NO: 2 or 11.

5. The method of claim 1, wherein the CDH6 is an amino acid sequence selected from the group consisting of SEQ ID NO: 12, 13, and 14.

6. The method of claim 1, wherein the CDH18 is an amino acid sequence selected from the group consisting of SEQ ID NO: 15, 16, and 17.

7. The method of claim 1, further comprising measuring apoptosis of CDH expressing cells in the presence of each of the identified test agents.

8. The method of claim 7, the CDH expressing cells are selected from the group consisting of kidney cancer cells, liver cancer cells, lung cancer cells, and colon cancer cells.

* * * * *